US012678603B2

(12) United States Patent
Fox et al.

(10) Patent No.: US 12,678,603 B2
(45) Date of Patent: Jul. 14, 2026

(54) DRUG DELIVERY SYSTEMS AND METHODS FOR TREATING THE NASAL CAVITY

(71) Applicant: Arrinex, Inc., Redwood City, CA (US)

(72) Inventors: William Jason Fox, San Mateo, CA (US); Brian Fahey, Menlo Park, CA (US); Mojgan Saadat, Atherton, CA (US); Vahid Saadat, Atherton, CA (US)

(73) Assignee: Arrinex, Inc., Redwood City, CA (US)

( * ) Notice: Subject to any disclaimer, the term of this patent is extended or adjusted under 35 U.S.C. 154(b) by 931 days.

(21) Appl. No.: 17/251,932

(22) PCT Filed: Jun. 14, 2019

(86) PCT No.: PCT/US2019/037292
§ 371 (c)(1),
(2) Date: Dec. 14, 2020

(87) PCT Pub. No.: WO2019/241697
PCT Pub. Date: Dec. 19, 2019

(65) Prior Publication Data
US 2021/0268243 A1    Sep. 2, 2021

Related U.S. Application Data

(60) Provisional application No. 62/684,917, filed on Jun. 14, 2018.

(51) Int. Cl.
*A61M 19/00*       (2006.01)
*A61B 17/3203*     (2006.01)
(Continued)

(52) U.S. Cl.
CPC ......... *A61M 31/00* (2013.01); *A61B 17/3203* (2013.01); *A61B 18/02* (2013.01);
(Continued)

(58) Field of Classification Search
CPC .......... A61M 19/00; A61M 2210/0681; A61M 25/0082; A61M 25/0084;
(Continued)

(56) References Cited

U.S. PATENT DOCUMENTS

| | | |
|---|---|---|
| 7,975,700 B2 | 7/2011 | Frazier et al. |
| 9,364,250 B2 | 6/2016 | Aljuri et al. |

(Continued)

FOREIGN PATENT DOCUMENTS

| | | |
|---|---|---|
| CN | 102905633 B | 6/2017 |
| EP | 1 474 203 B1 | 6/2016 |

(Continued)

OTHER PUBLICATIONS

International Search Report mailed on Oct. 11, 2019, issued in connection with International Application No. PCT/US2019/037292, filed on Jun. 14, 2019, 2 pages.
(Continued)

*Primary Examiner* — Emily L Schmidt
(74) *Attorney, Agent, or Firm* — McDonnell Boehnen Hulbert & Berghoff LLP

(57) ABSTRACT

In an example, a method for delivery of a therapeutic agent to at least one of a palatine canal or a pterygopalatine fossa of a patient is described. The method includes inserting a delivery device into a nasal cavity of a patient. The delivery device includes an elongated shaft with a proximal end and a distal end, a handpiece coupled to the proximal end of the elongated shaft, and a boring element disposed on the distal end of the elongated shaft. The method also includes advancing the distal end of the elongated shaft to a position proximate to a palatine bone within the nasal cavity, actuating the boring element to form a passage in the palatine
(Continued)

bone between the nasal cavity and a palatine canal of the patient, and delivering a therapeutic agent into the palatine canal.

12 Claims, 24 Drawing Sheets

(51) Int. Cl.
*A61B 18/02* (2006.01)
*A61M 31/00* (2006.01)
*A61B 18/00* (2006.01)
*A61M 25/00* (2006.01)

(52) U.S. Cl.
CPC .............. *A61B 2018/00327* (2013.01); *A61B 2018/00577* (2013.01); *A61B 2218/007* (2013.01); *A61M 19/00* (2013.01); *A61M 25/0084* (2013.01); *A61M 2210/0681* (2013.01)

(58) Field of Classification Search
CPC .. A61M 2025/0085; A61M 2025/0086; A61M 2025/0087; A61M 2025/0089; A61M 2025/009; A61M 2025/0092; A61M 2025/0093; A61M 2025/0095
See application file for complete search history.

(56) References Cited

U.S. PATENT DOCUMENTS

| | | | |
|---|---|---|---|
| 9,629,684 | B2 | 4/2017 | Jenkins et al. |
| 9,687,288 | B2 | 6/2017 | Saadat |
| 2004/0153111 | A1* | 8/2004 | Hosoada ........ A61B 17/320016 |
| | | | 604/48 |
| 2009/0118700 | A1* | 5/2009 | Callas ................ A61B 17/3478 |
| | | | 600/109 |
| 2013/0030545 | A1* | 1/2013 | Gross .................. A61M 27/002 |
| | | | 623/23.7 |
| 2013/0324911 | A1 | 12/2013 | Ohri et al. |
| 2015/0164571 | A1* | 6/2015 | Saadat ................. G01N 29/265 |
| | | | 600/109 |
| 2015/0306188 | A1 | 10/2015 | Bratbak et al. |
| 2016/0249796 | A1 | 9/2016 | Fujisaki |
| 2017/0056621 | A1 | 3/2017 | Stein et al. |
| 2017/0367724 | A1* | 12/2017 | Donnelly .......... A61B 17/3203 |
| 2018/0000553 | A1 | 1/2018 | Bratbak |
| 2019/0344048 | A1* | 11/2019 | Sawada ............. A61M 25/0084 |
| 2020/0297239 | A1* | 9/2020 | Olson .................. A61B 5/6852 |

FOREIGN PATENT DOCUMENTS

| | | |
|---|---|---|
| EP | 3 106 190 A1 | 12/2016 |
| JP | 2014-064779 | 4/2014 |
| JP | 2016-511085 | 4/2016 |
| JP | 2018-020125 | 2/2018 |
| WO | 2017139805 A1 | 8/2017 |

OTHER PUBLICATIONS

Written Opinion mailed on Oct. 11, 2019, issued in connection with International Application No. PCT/US2019/037292, filed on Jun. 14, 2019, 6 pages.

* cited by examiner

102S

102X

102I

102T

102W

102U

102I

102V

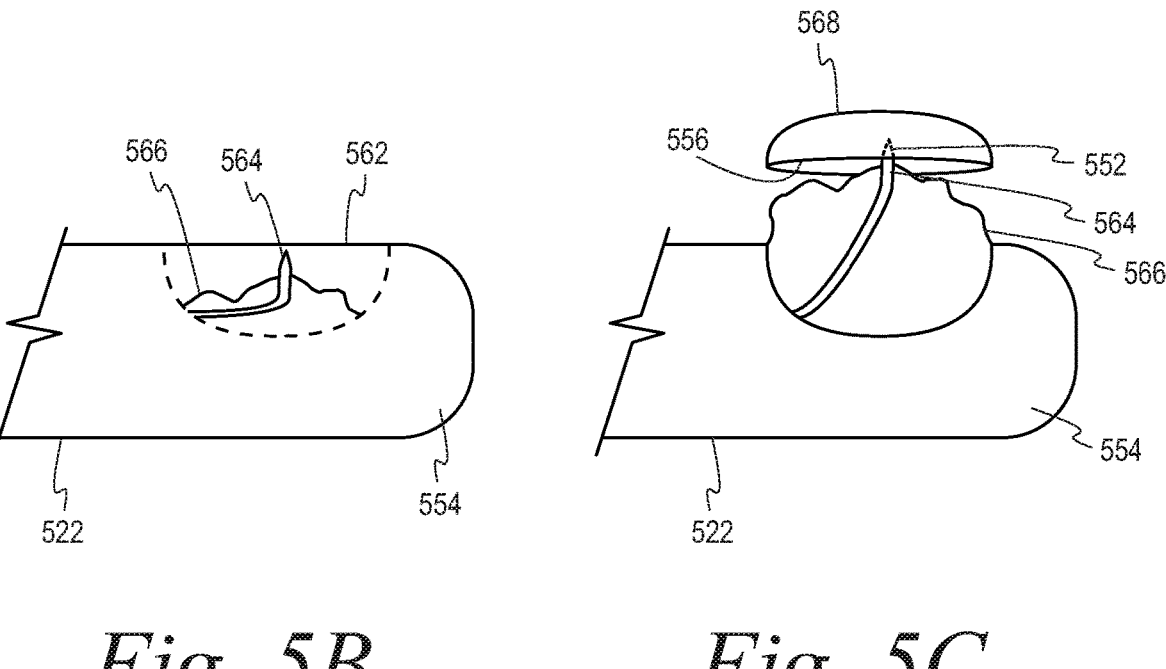
*Fig. 5B* *Fig. 5C*
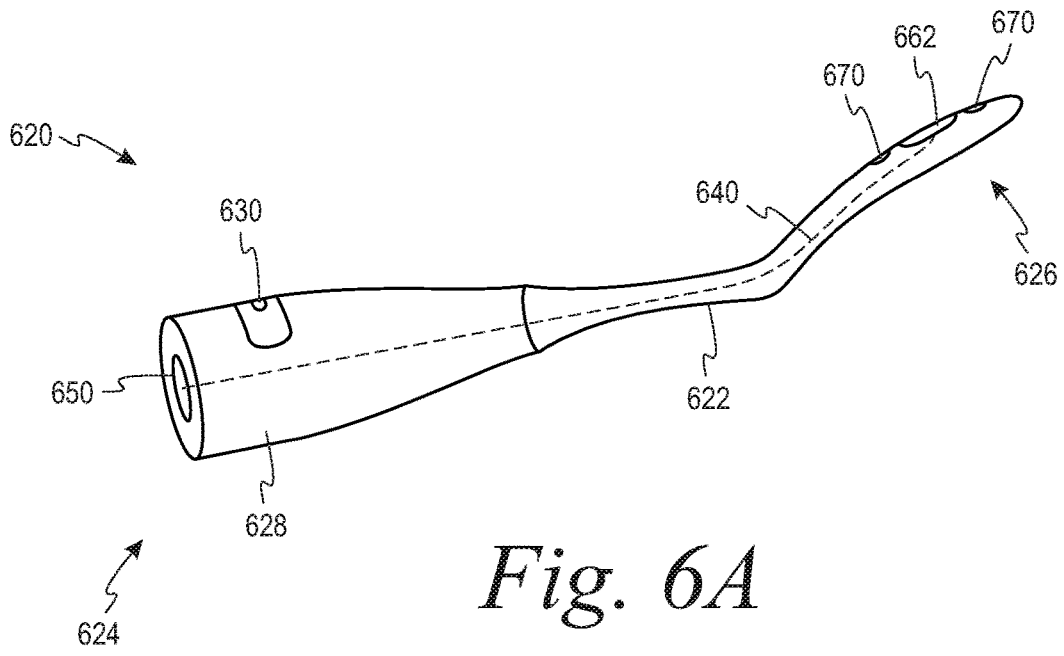
*Fig. 6A*

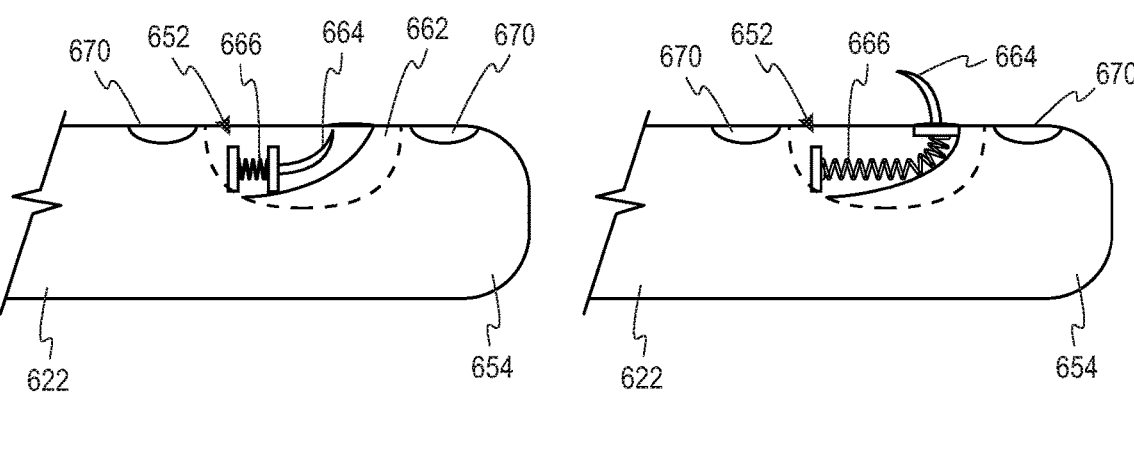
*Fig. 6B*          *Fig. 6C*
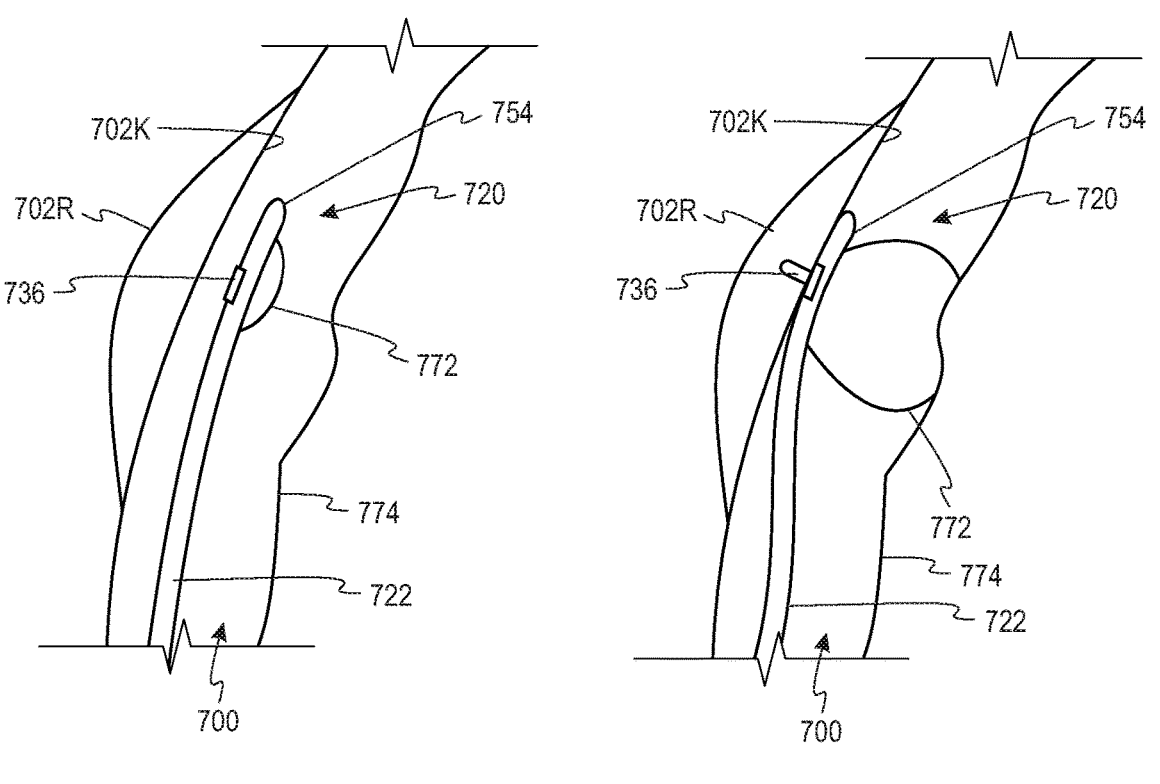
*Fig. 7A*          *Fig. 7B*

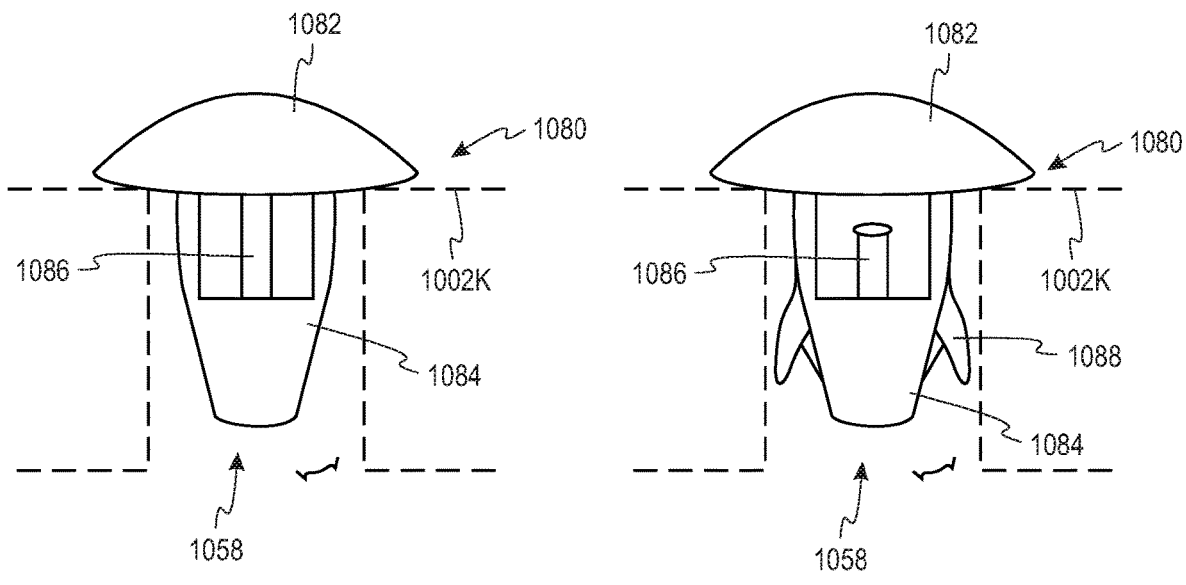
*Fig. 10A*          *Fig. 10B*
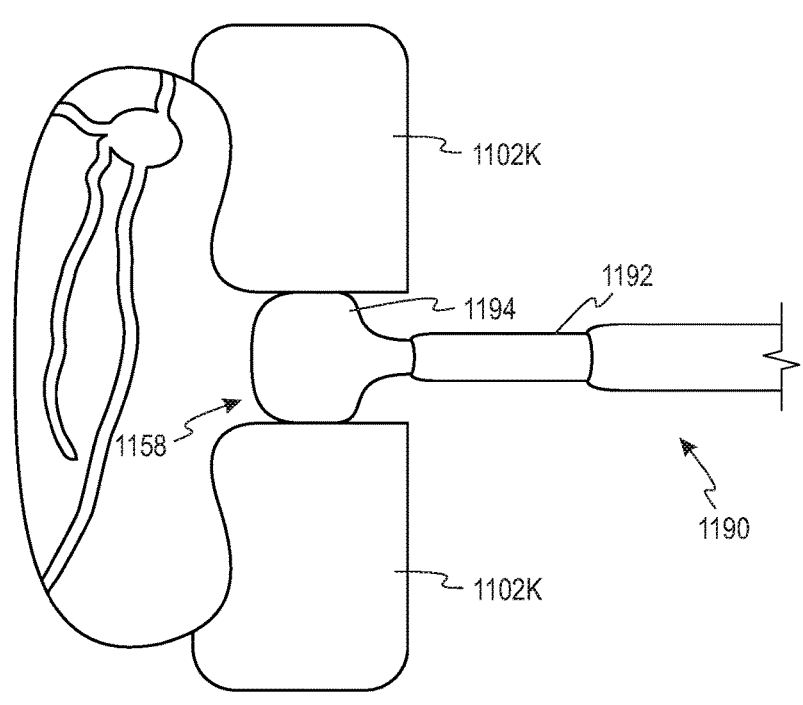
*Fig. 11*

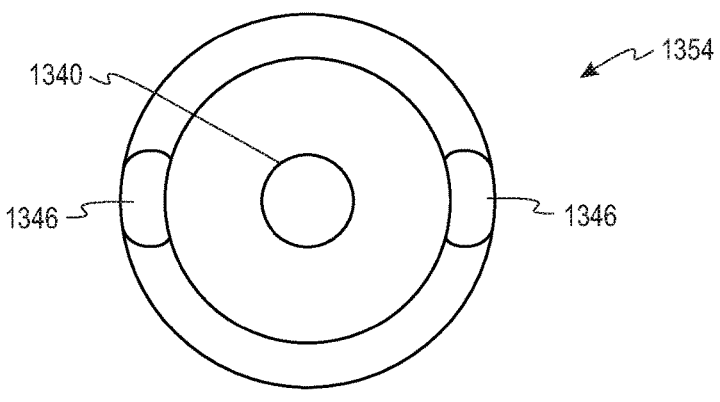
*Fig. 13B*
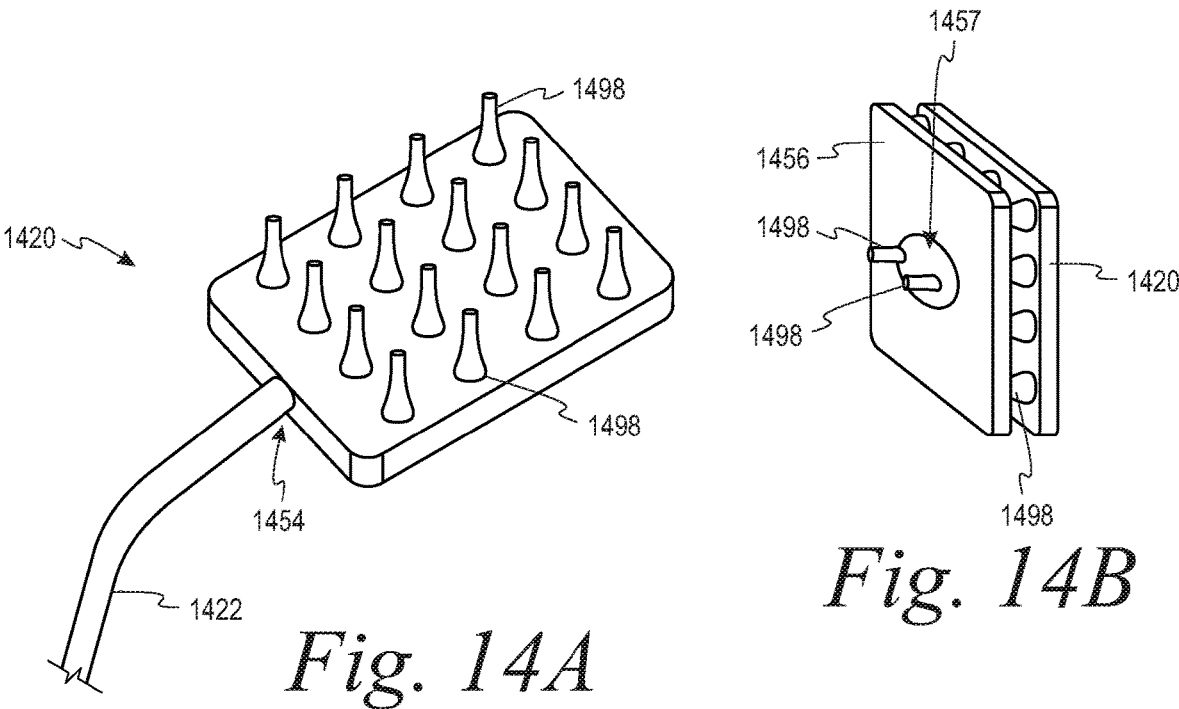
*Fig. 14A*
*Fig. 14B*

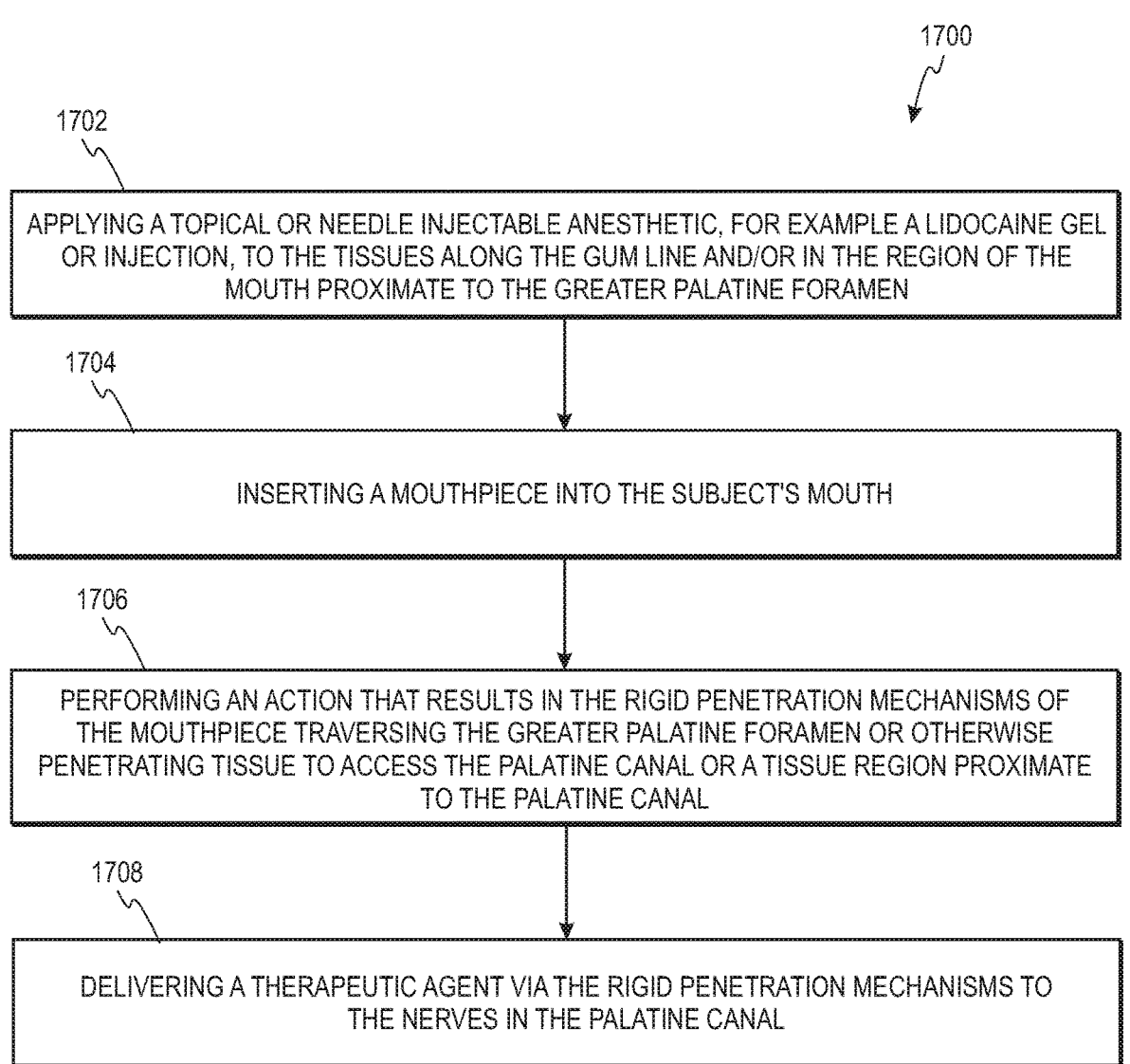

1700

1702

APPLYING A TOPICAL OR NEEDLE INJECTABLE ANESTHETIC, FOR EXAMPLE A LIDOCAINE GEL OR INJECTION, TO THE TISSUES ALONG THE GUM LINE AND/OR IN THE REGION OF THE MOUTH PROXIMATE TO THE GREATER PALATINE FORAMEN

1704

INSERTING A MOUTHPIECE INTO THE SUBJECT'S MOUTH

1706

PERFORMING AN ACTION THAT RESULTS IN THE RIGID PENETRATION MECHANISMS OF THE MOUTHPIECE TRAVERSING THE GREATER PALATINE FORAMEN OR OTHERWISE PENETRATING TISSUE TO ACCESS THE PALATINE CANAL OR A TISSUE REGION PROXIMATE TO THE PALATINE CANAL

1708

DELIVERING A THERAPEUTIC AGENT VIA THE RIGID PENETRATION MECHANISMS TO THE NERVES IN THE PALATINE CANAL

*Fig. 17*

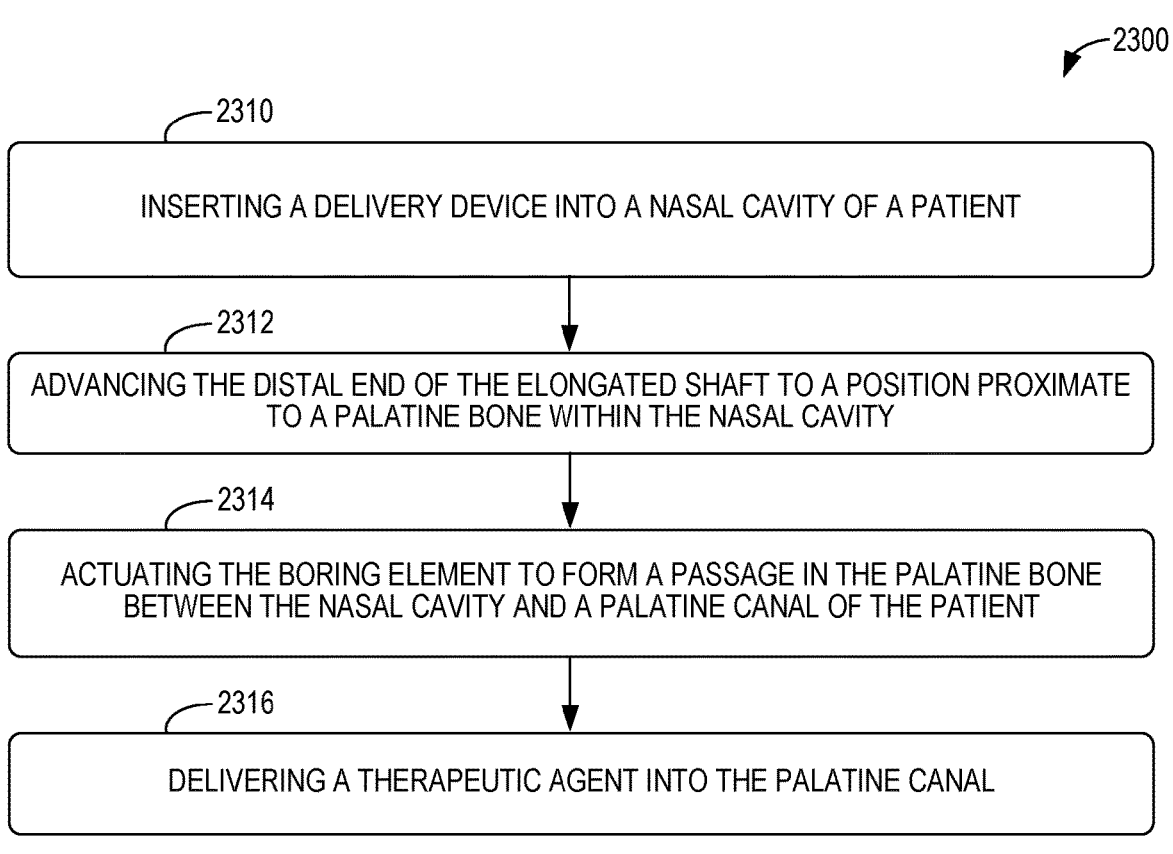

2300

2310

INSERTING A DELIVERY DEVICE INTO A NASAL CAVITY OF A PATIENT

2312

ADVANCING THE DISTAL END OF THE ELONGATED SHAFT TO A POSITION PROXIMATE TO A PALATINE BONE WITHIN THE NASAL CAVITY

2314

ACTUATING THE BORING ELEMENT TO FORM A PASSAGE IN THE PALATINE BONE BETWEEN THE NASAL CAVITY AND A PALATINE CANAL OF THE PATIENT

2316

DELIVERING A THERAPEUTIC AGENT INTO THE PALATINE CANAL

*Fig. 23*

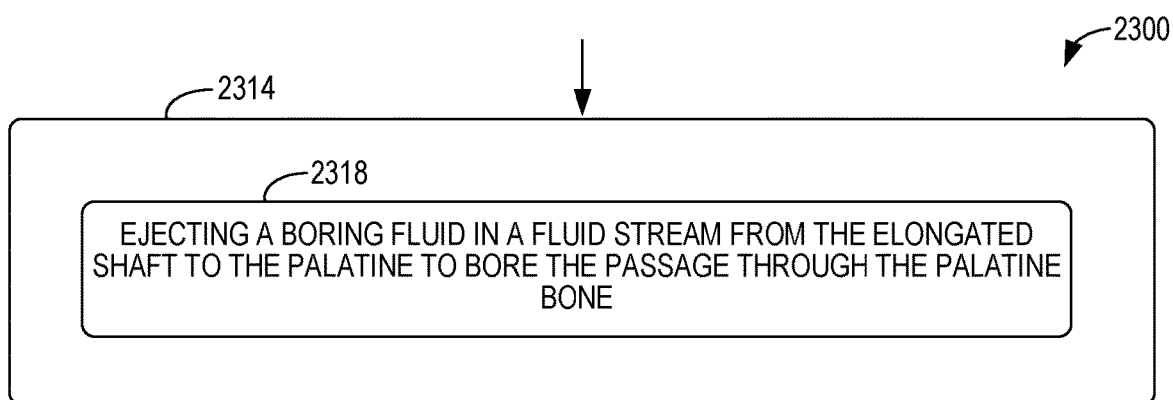

2300

2314

2318

EJECTING A BORING FLUID IN A FLUID STREAM FROM THE ELONGATED SHAFT TO THE PALATINE TO BORE THE PASSAGE THROUGH THE PALATINE BONE

*Fig. 24*

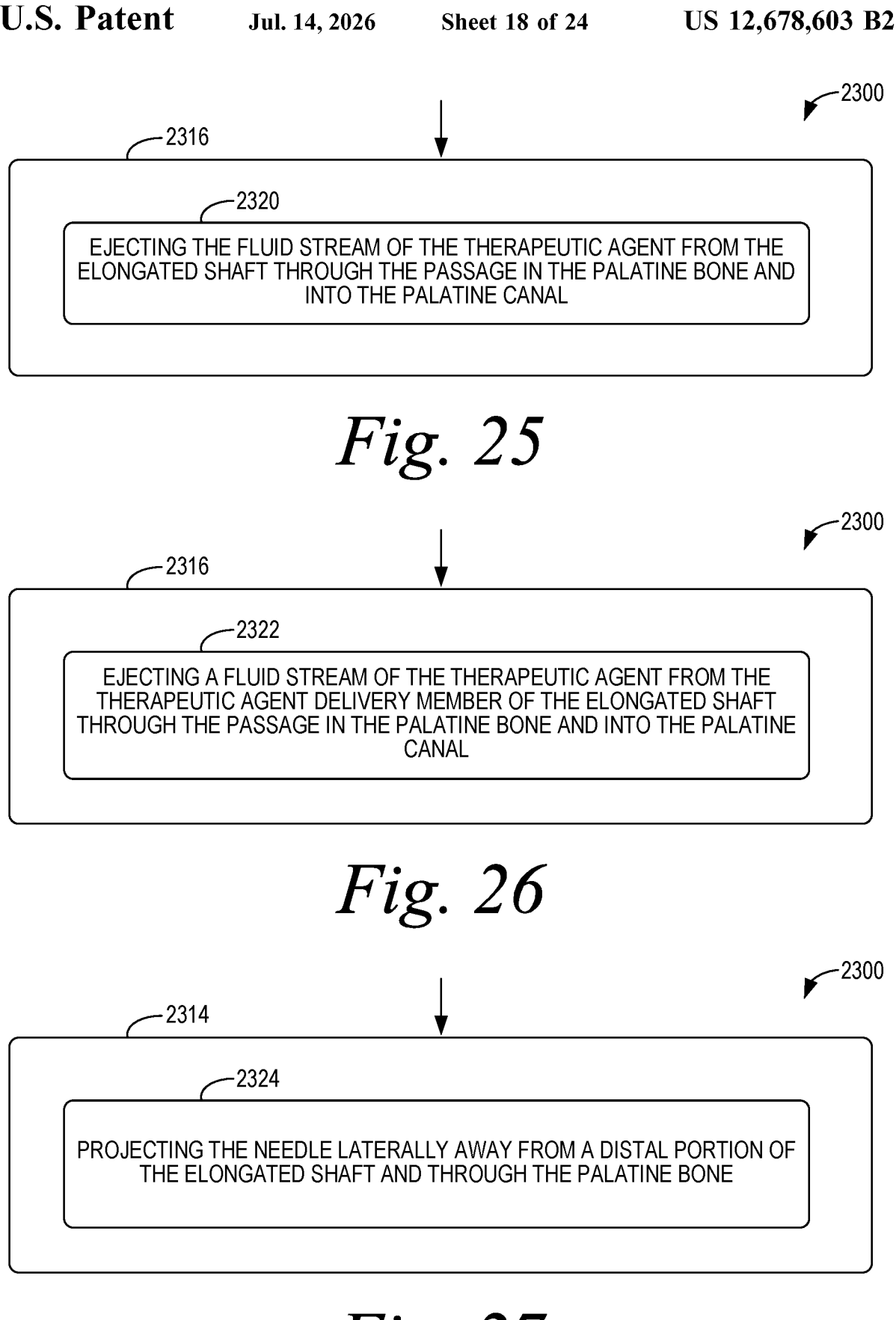

─2300

─2316

─2320

EJECTING THE FLUID STREAM OF THE THERAPEUTIC AGENT FROM THE ELONGATED SHAFT THROUGH THE PASSAGE IN THE PALATINE BONE AND INTO THE PALATINE CANAL

EJECTING A FLUID STREAM OF THE THERAPEUTIC AGENT FROM THE THERAPEUTIC AGENT DELIVERY MEMBER OF THE ELONGATED SHAFT THROUGH THE PASSAGE IN THE PALATINE BONE AND INTO THE PALATINE CANAL

PROJECTING THE NEEDLE LATERALLY AWAY FROM A DISTAL PORTION OF THE ELONGATED SHAFT AND THROUGH THE PALATINE BONE

INFLATING AN EXPANDABLE MEMBER COUPLED TO THE NEEDLE

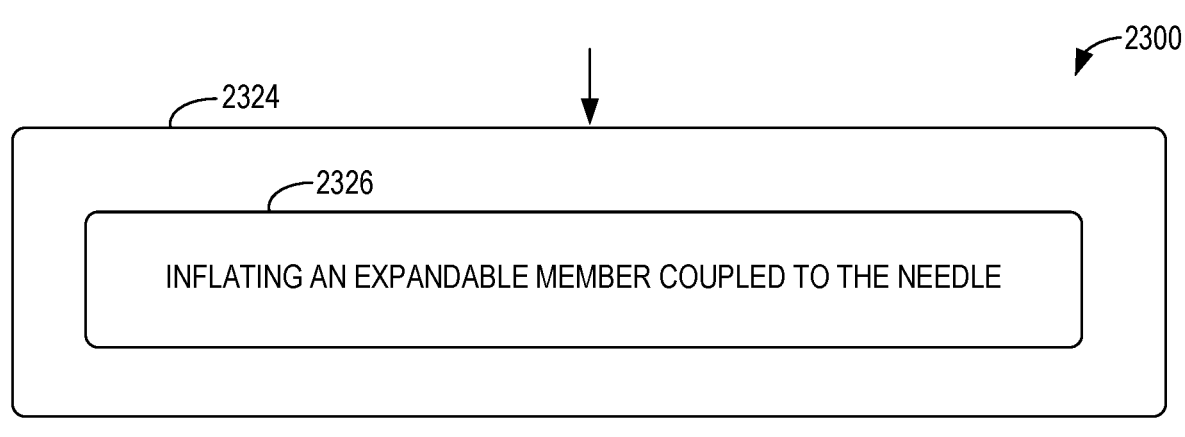

RELEASING A COMPRESSED SPRING COUPLED TO THE NEEDLE

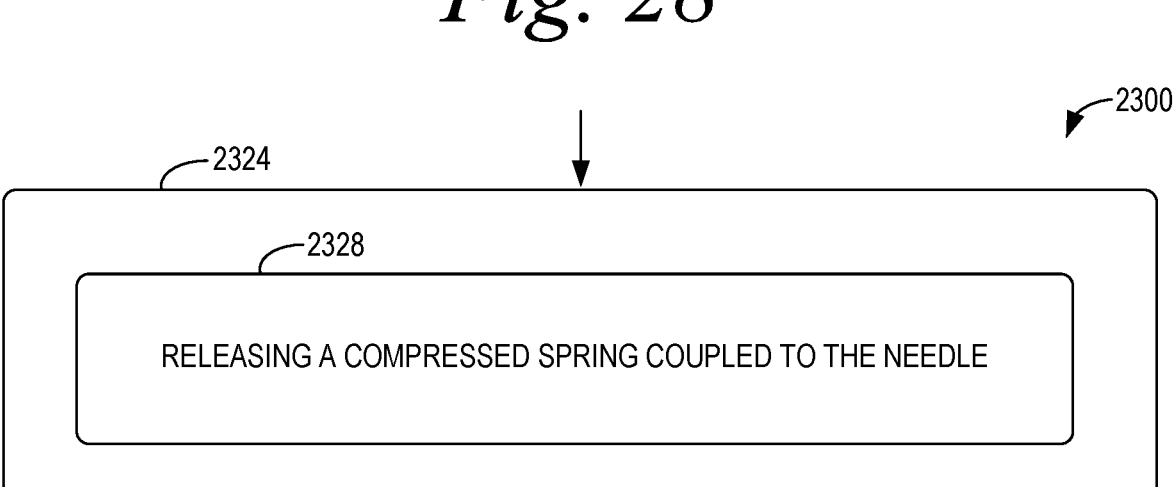

PRIOR TO ACTUATING THE BORING ELEMENT, POSITIONING THE DISTAL END OF THE
ELONGATED SHAFT SUCH THAT THE BORING ELEMENT IS ADJACENT TO THE PALATINE
BONE BY INFLATING AN EXPANDABLE MEMBER COUPLED TO THE DISTAL END OF THE
ELONGATED SHAFT SO AS TO STABILIZE THE NEEDLE WHILE THE NEEDLE
PENETRATES THROUGH THE PALATINE BONE

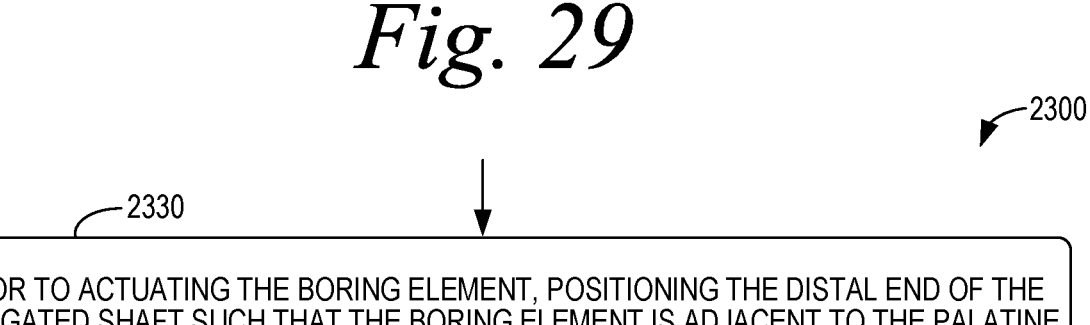

INSERTING THE DELIVERY CONDUIT THROUGH THE PASSAGE IN THE PALATINE BONE AND INTO THE PALATINE CANAL

2334

EJECTING THE THERAPEUTIC AGENT THROUGH THE DELIVERY CONDUIT AND DIRECTLY INTO THE PALATINE CANAL

2300

2336

POSITIONING A PLUG WITHIN THE PASSAGE AFTER THE THERAPEUTIC AGENT IS DELIVERED TO CLOSE THE PASSAGE

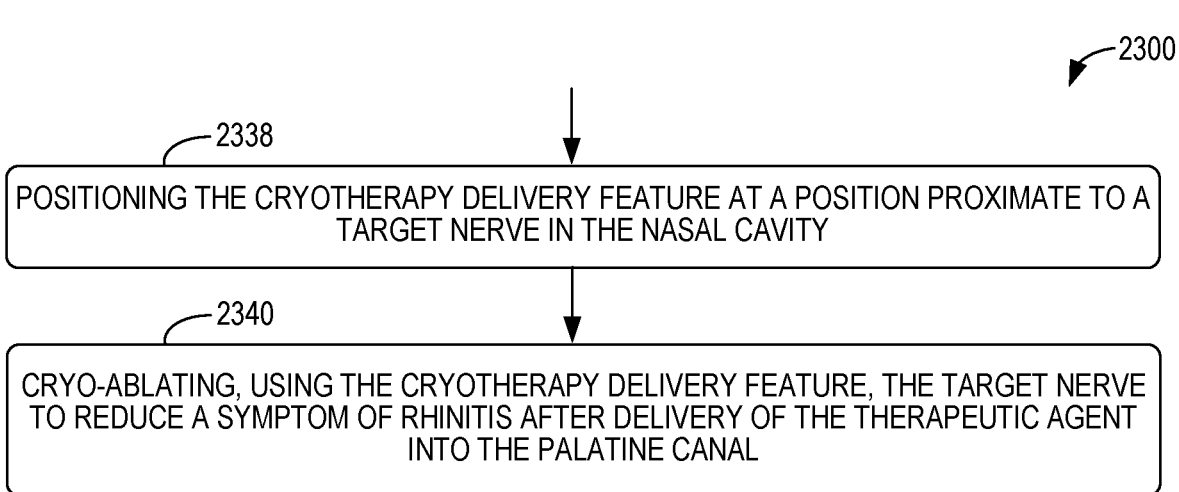

2300

2338

POSITIONING THE CRYOTHERAPY DELIVERY FEATURE AT A POSITION PROXIMATE TO A TARGET NERVE IN THE NASAL CAVITY

2340

CRYO-ABLATING, USING THE CRYOTHERAPY DELIVERY FEATURE, THE TARGET NERVE TO REDUCE A SYMPTOM OF RHINITIS AFTER DELIVERY OF THE THERAPEUTIC AGENT INTO THE PALATINE CANAL

*Fig. 33*

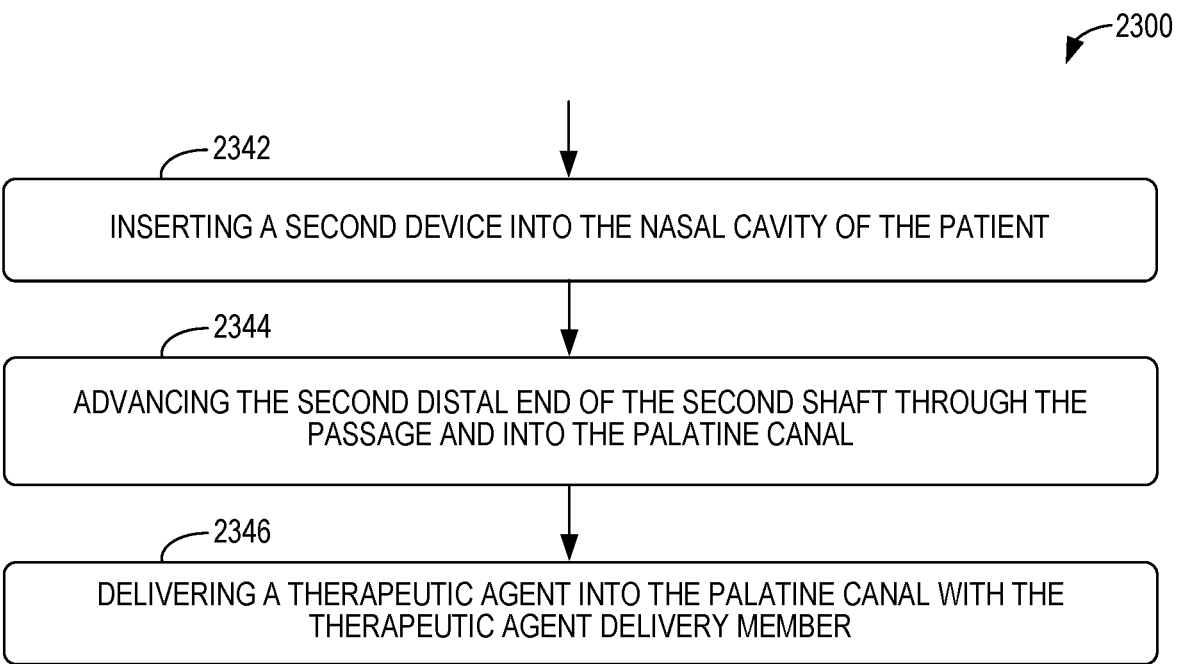

2300

2342

INSERTING A SECOND DEVICE INTO THE NASAL CAVITY OF THE PATIENT

2344

ADVANCING THE SECOND DISTAL END OF THE SECOND SHAFT THROUGH THE PASSAGE AND INTO THE PALATINE CANAL

2346

DELIVERING A THERAPEUTIC AGENT INTO THE PALATINE CANAL WITH THE THERAPEUTIC AGENT DELIVERY MEMBER

*Fig. 34*

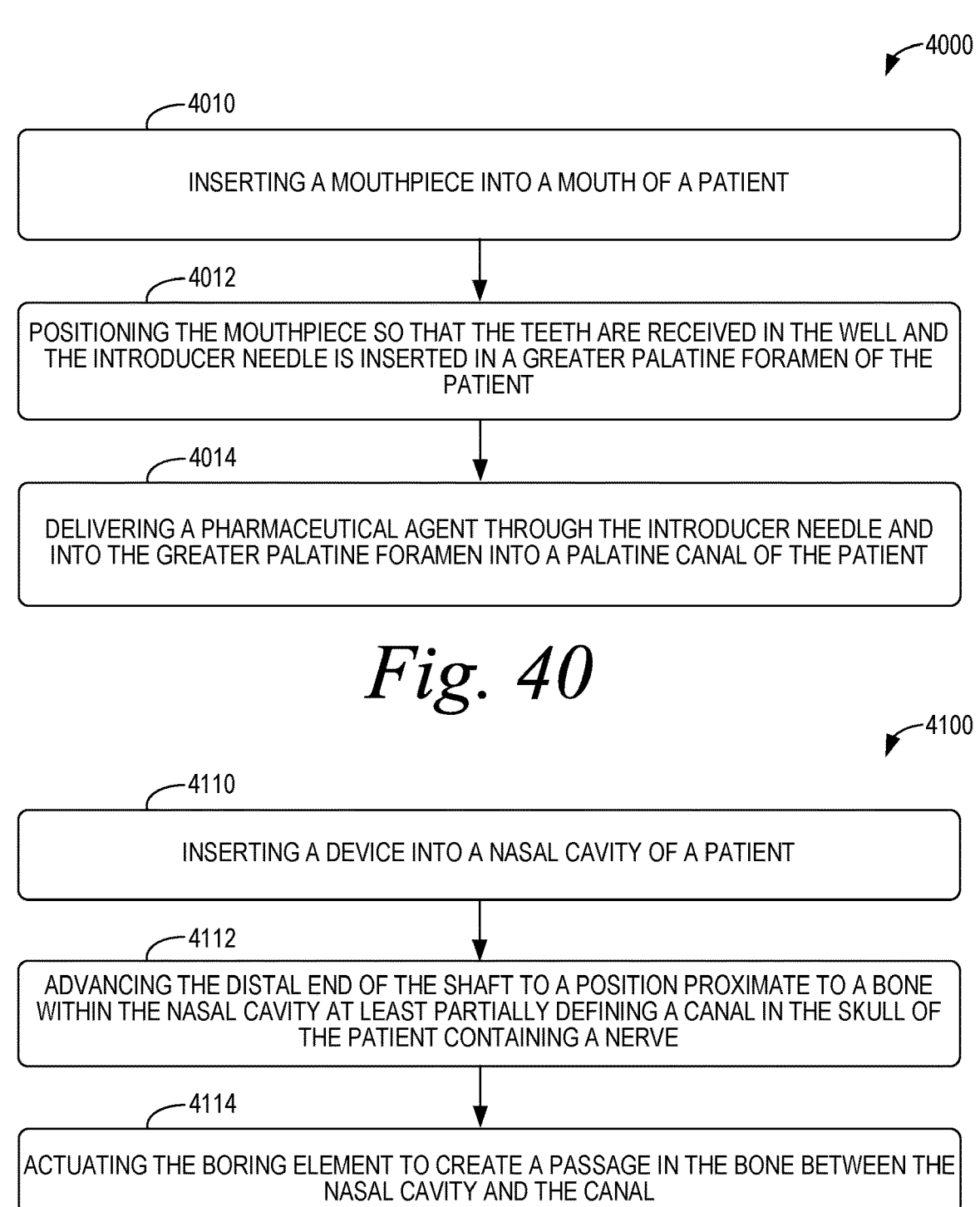

4000

4010

INSERTING A MOUTHPIECE INTO A MOUTH OF A PATIENT

4012

POSITIONING THE MOUTHPIECE SO THAT THE TEETH ARE RECEIVED IN THE WELL AND THE INTRODUCER NEEDLE IS INSERTED IN A GREATER PALATINE FORAMEN OF THE PATIENT

4014

DELIVERING A PHARMACEUTICAL AGENT THROUGH THE INTRODUCER NEEDLE AND INTO THE GREATER PALATINE FORAMEN INTO A PALATINE CANAL OF THE PATIENT

INSERTING A DEVICE INTO A NASAL CAVITY OF A PATIENT

4112

ADVANCING THE DISTAL END OF THE SHAFT TO A POSITION PROXIMATE TO A BONE WITHIN THE NASAL CAVITY AT LEAST PARTIALLY DEFINING A CANAL IN THE SKULL OF THE PATIENT CONTAINING A NERVE

4114

ACTUATING THE BORING ELEMENT TO CREATE A PASSAGE IN THE BONE BETWEEN THE NASAL CAVITY AND THE CANAL

4116

DELIVERING A THERAPEUTIC AGENT INTO THE CANAL

*Fig. 41*

DRUG DELIVERY SYSTEMS AND METHODS FOR TREATING THE NASAL CAVITY

CROSS-REFERENCE TO RELATED APPLICATIONS

The present application is the US national phase under 35 U.S.C. § 371 of International Application No. PCT/US2019/037292, filed Jun. 14, 2019, which claims benefit of U.S. Provisional Application No. 62/684,917, filed Jun. 14, 2018, the contents of which is are hereby incorporated by reference in its their entirety.

The present application is related to U.S. application Ser. No. 15/693,216, filed Aug. 31, 2017; U.S. application Ser. No. 15/786,306, filed Oct. 17, 2017; U.S. application Ser. No. 15/682,804, filed Aug. 22, 2017; U.S. application Ser. No. 15/431,740, filed Feb. 13, 2017; U.S. application Ser. No. 15/624,632, filed Jun. 15, 2017; U.S. Provisional Application No. 62/861,591, filed Jun. 14, 2019, each of which is incorporated by reference herein in its entirety.

FIELD

The present invention is related to systems, devices and methods for delivering a therapeutic agent into a bony cavity. More particularly, the present invention relates to delivering a therapeutic agent into a palatine canal of a patient. The therapeutic agent may be an anesthetic agent and may be used in relation to the treatment of rhinitis.

BACKGROUND

FIGS. 1A-1B depict an anatomy of a nasal cavity 100. In particular, FIG. 1A depicts a sagittal planar view of a lateral wall of the nasal cavity 100 including a number of bony structures in the region. More particularly, FIG. 1A depicts a nasal bone 102A, a frontal process of maxilla 102B, a lacrimal bone 102C, a superior concha 102D, a middle concha 102E, a uncinate process of ethmoid 102F, a sphenopalatine foramen 102G, a posterior fontanelle 102H, greater palatine and lesser palatine nerves 102I, a medial pterygoid plate of sphenoid bone 102J, a perpendicular plate of palatine bone 102K, an inferior concha 102L, a greater palatine nerve 102M, a minor alar cartilage 102N, a major alar cartilage 102O, a lateral process of septal cartilage 102P. FIG. 1B depicts a similar view where a small section of bone has been removed to show the palatine canal and the pterygopalatine fossa. FIG. 1B shows a plurality of nasal nerves. In particular, FIG. 1B shows the greater and lesser palatine nerves 102I, a pterygopalatine ganglion 102Q, and a palatine canal 102R. FIG. 1C depicts an inferior view of an oral cavity palate showing the palatine foramen, which are openings of the palatine canal in the hard palate where notable nerves and blood vessels course from the canal along the roof of the mouth. For instance, FIG. 1C shows an incisive fossa 102S, a greater palatine nerve 102I, a greater palatine foramen 102T, a lesser palatine foramen 102U, a lesser palatine nerve 102I, an uvula 102V, a lesser palatine artery 102W, and a greater palatine artery 102X.

As shown FIG. 1A, a sphenopalatine foramen 102G is a small opening near the superior aspect of the palatine bone 102K where the sphenopalatine artery and the posterior nasal nerves traverse into the nasal cavity 100. The sphenopalatine foramen 102G and the palatine foramen 102T, 102U provide an access point to the pterygopalatine fossa and palatine canal 102R where the sphenopalatine ganglion, maxillary nerve, and the root of the sphenopalatine artery resides. Although challenging, accessing and delivering a therapeutic agent to the fossa and/or the palatine canal 102R can enable a physician to have better control of pain and bleeding during surgical procedures in awake patients. An example but not limited to are surgical procedures within the nasal cavity 100. In-office surgical procedures within the nasal cavity 100 in awake patients are becoming more and more prevalent and the success of these procedures is based in-part on how well the patient can tolerate the procedure and how well the physician can visualize the treatment that is being performed.

Currently, many physicians achieve local pain control and bleeding during these procedures by topically applying an anesthetic agent and/or a vasoconstricting agent onto the mucosa in the nasal cavity or by injecting these agents directly into the mucosa. In some cases, physicians will inject under the mucosa near the sphenopalatine foramen, creating a large bleb in the attempt to have the agents migrate into the foramen and be absorbed by the trunks of the posterior nasal nerves and/or sphenopalatine artery. Both of these options have been proven effective for controlling the pain and bleeding proximate to the immediate location of application, but have their limitations achieving reliable, adequate widespread control due to the large degree of spreading of the vessels and nerves that exists in the nasal cavity.

SUMMARY

In an example, a method for delivery of a therapeutic agent to at least one of a palatine canal or a pterygopalatine fossa of a patient is described. The method includes inserting a delivery device into a nasal cavity of a patient. The delivery device includes an elongated shaft with a proximal end and a distal end, a handpiece coupled to the proximal end of the elongated shaft, and a boring element disposed on the distal end of the elongated shaft. The method also includes advancing the distal end of the elongated shaft to a position proximate to a palatine bone within the nasal cavity, actuating the boring element to form a passage in the palatine bone between the nasal cavity and a palatine canal of the patient, and delivering a therapeutic agent into the palatine canal.

In another example, a method for delivering a therapeutic agent to at least one of a palatine canal or a pterygopalatine fossa of a patient is described. The method includes inserting a device into a mouth of a patient. The device includes an elongated shaft with a proximal end and a distal end, an access port coupled to the proximal end of the elongated shaft, and a therapeutic agent delivery member disposed at a distal portion of the elongated shaft. The therapeutic agent delivery member includes a delivery conduit. The method also includes advancing the distal end of the elongated shaft of the device to a position proximate to a greater palatine foramen in the mouth of the patient. The method further includes delivering, using the delivery conduit, a therapeutic agent into the at least one of a palatine canal or a pterygopalatine fossa with the therapeutic agent delivery member.

In another example, a method for delivering a therapeutic agent to at least one of a palatine canal or a pterygopalatine fossa of a patient is described. The method includes inserting a mouthpiece into a mouth of a patient. The mouthpiece is u-shaped. The mouthpiece includes a well configured to receive teeth of the patient. The mouthpiece includes an introducer needle. The method also includes positioning the mouthpiece so that the teeth are received in the well and the introducer needle is inserted in a greater palatine foramen of the patient. The method further includes delivering a pharmaceutical agent through the introducer needle and into the greater palatine foramen into a palatine canal of the patient.

The features, functions, and advantages that have been discussed can be achieved independently in various examples or may be combined in yet other examples further details of which can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 6A shows a delivery device, according to another example.

FIG. 6B shows a distal end of the delivery device shown in FIG. 6A with a spring in a compressed state, according to an example.

FIG. 6C shows the distal end of the delivery device shown in FIG. 6A with the spring in a released state, according to an example.

FIG. 7A shows a delivery device with an expandable member in a collapsed state, according to another example.

FIG. 7B shows a distal end of the delivery device shown in FIG. 7A with the expandable member in an expanded state, according to an example.

FIG. 10A shows a cap in a first state, according to another example.

FIG. 10B shows the cap in a second state, according to another example.

FIG. 11 shows a nasal tool and a plug, according to an example.

FIG. 13B shows a distal end of the delivery device shown in FIG. 13A, according to an example.

FIG. 14A shows a delivery device, according to another example.

FIG. 14B shows the delivery device shown in FIG. 14A with protrusions extending through an opening in a tissue or a bony structure, according to an example.

FIG. 17 shows a flowchart for a method of delivering a therapeutic agent, according to another example.

FIG. 23 shows a method for delivery of a therapeutic agent to at least one of a palatine canal or a pterygopalatine fossa of a patient according to an example.

FIG. 24 shows a method for delivery of a therapeutic agent to at least one of a palatine canal or a pterygopalatine fossa of a patient that can be used with the method of FIG. 23, according to an example.

FIG. 25 shows a method for delivery of a therapeutic agent to at least one of a palatine canal or a pterygopalatine fossa of a patient that can be used with the method of FIG. 24, according to an example.

FIG. 26 shows a method for delivery of a therapeutic agent to at least one of a palatine canal or a pterygopalatine fossa of a patient that can be used with the method of FIG. 24, according to an example.

FIG. 27 shows a method for delivery of a therapeutic agent to at least one of a palatine canal or a pterygopalatine fossa of a patient that can be used with the method of FIG. 23, according to an example.

FIG. 28 shows a method for delivery of a therapeutic agent to at least one of a palatine canal or a pterygopalatine fossa of a patient that can be used with the method of FIG. 27, according to an example.

FIG. 29 shows a method for delivery of a therapeutic agent to at least one of a palatine canal or a pterygopalatine fossa of a patient that can be used with the method of FIG. 27, according to an example.

FIG. 30 shows a method for delivery of a therapeutic agent to at least one of a palatine canal or a pterygopalatine fossa of a patient that can be used with the method of FIG. 27, according to an example.

FIG. 33 shows a method for delivery of a therapeutic agent to at least one of a palatine canal or a pterygopalatine fossa of a patient that can be used with the method of FIG. 23, according to an example.

FIG. 34 shows a method for delivery of a therapeutic agent to at least one of a palatine canal or a pterygopalatine fossa of a patient that can be used with the method of FIG. 23, according to an example.

FIG. 40 shows a method for delivery of a therapeutic agent to at least one of a palatine canal or a pterygopalatine fossa of a patient according to another example.

FIG. 41 shows a method for delivery of a therapeutic agent to a canal in a skull of a patient containing a nerve according to an example.

DETAILED DESCRIPTION

Figure 1A:
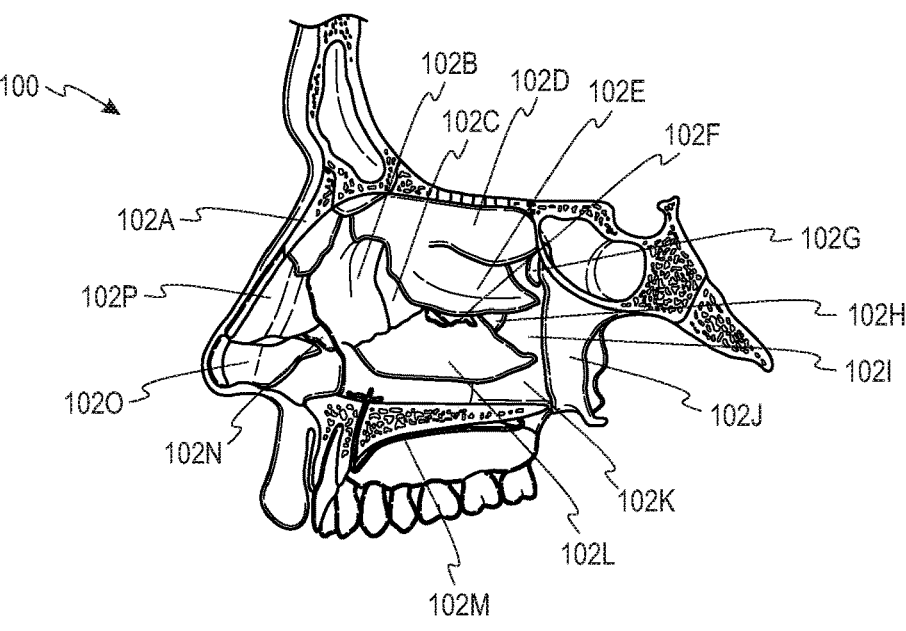
FIG. 1A shows anatomical structures in the nasal cavity and mouth.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

The present technology relates to systems, devices and methods for delivery of a therapeutic agent into the palatine canal. In examples, delivery of the therapeutic agent is achieved through penetration of the thin palatine bone 102K and creating a passage directly from the nasal cavity into the palatine canal through which an agent may be delivered. While the examples described disclose systems and methods for accessing the palatine canal via the deployment of an action to the palatine bone 102K, the technology may also be applied to other anatomical regions.

In examples, access to the palatine canal is achieved via the application of a stream of fluid applied at a high pressure to the mucosal wall in the nasal cavity in the region where the palatine bone 102K covers the palatine canal. The high pressure fluid jet bores a small hole through the mucosa and bone, providing a pathway for access to the palatine canal and the nerves located within the palatine canal. In examples, the fluid used in the boring process is also a therapeutic agent intended for delivery to the palatine canal. In examples, a non-toxic fluid such as water or saline is utilized to bore the passage to the palatine canal, and a therapeutic agent is subsequently delivered via this passage. In examples, access the palatine canal and pterygopalatine fossa to apply anesthesia or another therapeutic agent to the nerves and/or blood vessels within the canal is performed without penetration of a bone. For example, a transmucosal injection or a natural opening such as a foramen (e.g., the sphenopalatine foramen or the greater palatine foramen) can be used to access the palatine canal to deliver a therapeutic agent.

With the methods and apparatus described within this application, a physician is enabled to more reliably control pain and bleeding by delivering therapeutic agents into the anatomical regions where nasal nerves and relevant blood vessels originate. Delivery of agents to the pterygopalatine fossa and through the palatine canal and the associated potential benefits have been disclosed in the past (i.e. Douglas and Wormald: Pterygopalatine Fossa Infiltration, Laryngoscope 116: July 2006); however, the technique hasn't been widely adopted due to the complexity of accessing these regions and the potential safety issues. Current methods of access could cause damage to the sphenopalatine and palatine arteries, and may be accompanied by the risk of unintentionally injecting the therapeutic agents into the blood stream. The inventions disclosed within this application explain methods and features to reduce these risks and simplify the delivery process.

Figure 2:
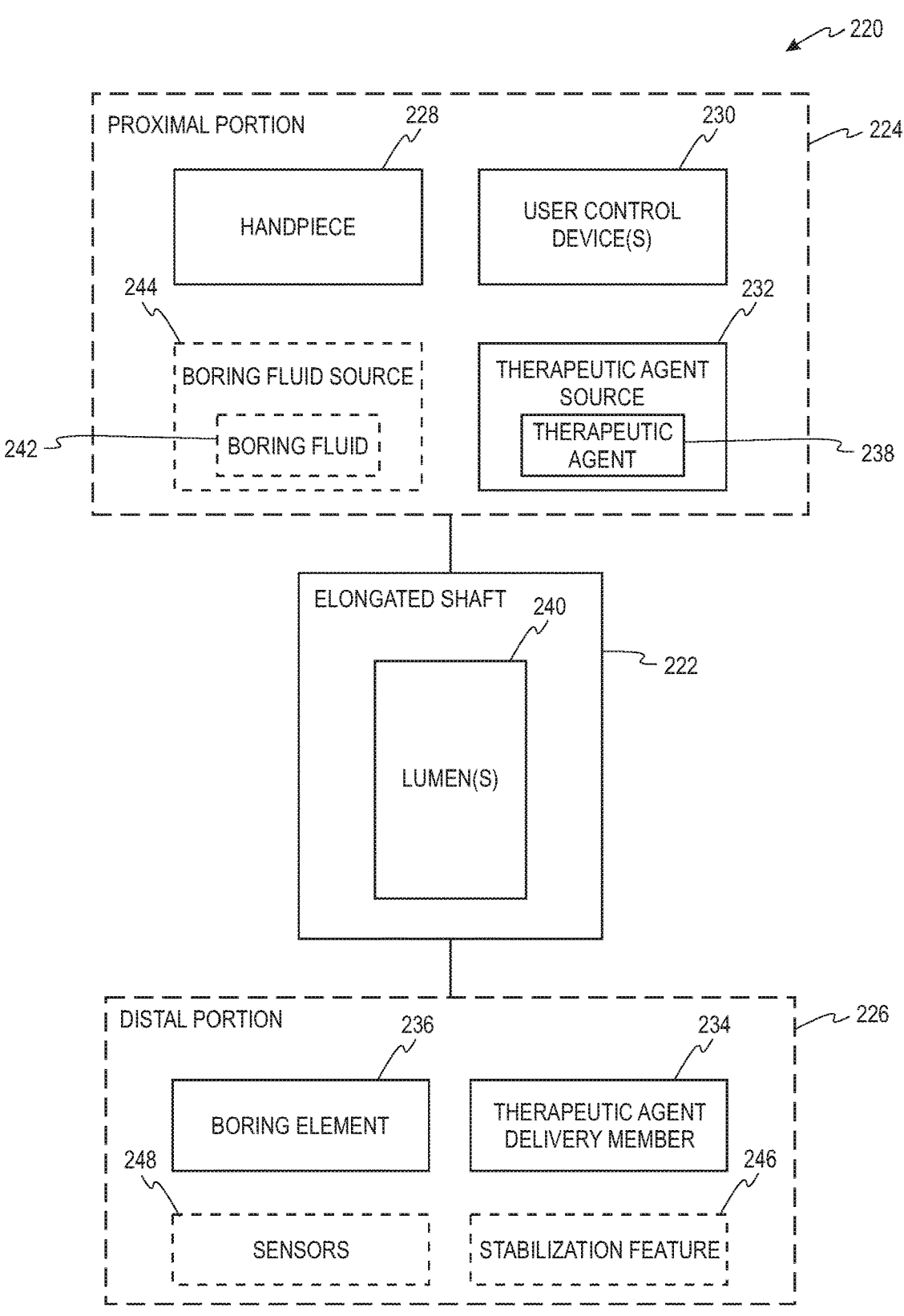
FIG. 2 shows a simplified block diagram of a delivery device, according to an example.

FIG. 2 depicts a simplified block diagram of a therapeutic agent delivery device 220 (hereinafter referred to as the "delivery device" for brevity), according to an example. As shown in FIG. 2, the delivery device 220 includes an elongated shaft 222 that extends between a proximal portion 224 of the delivery device 220 and a distal portion 226 of the delivery device 220. The elongated shaft 222 can be configured to be at least partially inserted in a nasal cavity of a patient. For example, the elongated shaft 222 can have a diameter between approximately 1 millimeters (mm) and approximately 4 mm. Additionally, for example, the elongated shaft 222 can be made from stainless steel, and/or a semi-rigid polymer (e.g., such as Nylon or Pebax).

Although the elongated shaft 222 is shown as being separate from the proximal portion 224 and the distal portion 226 in FIG. 2, the proximal portion 224 and/or the distal portion 226 of the delivery device 220 can include respective portions of the elongated shaft 222. More generally, the proximal portion 224 can include one or more components of the delivery device 220 that are located relatively farther away from a target tissue to be treated with a therapeutic agent while applying the therapeutic agent to the target tissue, and the distal portion 226 can include one or more components of the delivery device 220 that are located relatively closer to the target tissue while applying the therapeutic agent to the target tissue. As used herein, the term "target tissue" means a tissue that is to be treated with the therapeutic agent during a medical procedure.

The proximal portion 224 can include a handpiece 228, one or more user control devices 230 (e.g., one or more triggers, one or more knobs, one or more triggers, one or more buttons, one or more switches, one or more levers, and/or one or more dials), a therapeutic agent source 232, and/or other features. The distal portion 226 can include a therapeutic agent delivery member 234 and/or a boring element 236.

Within examples, the handpiece 228 can be configured to facilitate gripping and manipulating the delivery device 220. For instance, the handpiece 228 can have a shape and/or a size that can facilitate a user manipulating the elongated shaft 222 and the distal portion 226 using a single hand. In one example, the handpiece 228 can have a shape and/or a size that facilitates the user holding the handpiece 228 in a pistol gripping manner (e.g., the handpiece 228 can have an axis that is transverse to an axis of the elongated shaft 222). In another example, the handpiece 228 can additionally or alternatively have a shape and/or a size that facilitates the user holding the handpiece 228 in a writing utensil gripping manner (e.g., the handpiece 228 can have an axis that is substantially parallel to an axis of the elongated shaft 222). Additionally or alternatively, the handpiece 228 can (i) facilitate gripping and manipulating the delivery device 220 by having a shape and/or a size that is greater than a shape and/or a size of the elongated shaft 222 and/or (ii) allow the user to operate the user control device(s) 230 while gripping and manipulating the delivery device 220 with a single hand.

The therapeutic agent source 232 can store a therapeutic agent 238. As examples, the therapeutic agent 238 can include formulations of lidocaine, marcaine, tetracaine, bupivacaine, cocaine, another anesthetic, an antibiotic, a neurotoxin, and/or other therapeutic agents used during medical procedures. Also, the therapeutic agent 238 can be a gel, a foam, a mist, a powder, and/or a bioabsorbable solid.

As shown in FIG. 2, the elongated shaft 222 can include one or more lumens 240 that couple the therapeutic agent source 232 at the proximal portion 224 to the therapeutic agent delivery member 234 at the distal portion 226. The therapeutic agent delivery member 234 can be configured to deliver the therapeutic agent 238 to the target tissue. For example, the therapeutic agent delivery member 234 can include an exit port (i) in the lumen(s) 240 and/or the elongated shaft 222 at the distal portion 226, and (ii) configured to egress the therapeutic agent 238 from the lumen(s) 240 to the target tissue.

Within examples, the user control device(s) 230 can control a flow of the therapeutic agent 238 from the therapeutic agent source 232 to the therapeutic agent delivery member 234. For instance, the user control device(s) 230 can include one or more knobs, one or more triggers, one or more buttons, one or more switches, one or more levers, and/or one or more dials that can be actuated to start, stop, increase, and/or decrease a flow of the therapeutic agent 238 from the therapeutic agent source 232 to the therapeutic agent delivery member 234. Also, within examples, the user control device(s) 230 can be located on the handpiece 228 and/or at a location that is separate from the handpiece 228.

In some examples, the therapeutic agent source 232 can be separate from the handpiece 228. For instance, the therapeutic agent source 232 can include a syringe that contains the therapeutic agent 238. The syringe can be coupled to an infusion port on the handpiece 228 and a plunger of the syringe can be actuated to supply the therapeutic agent 238 from the therapeutic agent source 232 to the therapeutic agent delivery member 234 (e.g., via the lumen(s) 240) and from the therapeutic agent delivery member 234 to the target tissue. Thus, in this implementation, the therapeutic agent source 232 can provide a fluid pressure for delivering the therapeutic agent 238 through the lumen(s) 240 and out the therapeutic agent delivery member 234 to the target tissue.

In other examples, the therapeutic agent source 232 can be integrated with the handpiece 228 and/or actuated by the user control device(s) 230. For instance, in one implementation, the therapeutic agent source 232 can be a disposable reservoir or a reusable reservoir that is housed in the handpiece 228. The therapeutic agent source 232 can also include one or more valves and/or one or more pumps that facilitate supplying the therapeutic agent 238 from the therapeutic agent source 232 to the therapeutic agent delivery member 234. The valve(s) and/or the pump(s) can be operable by the user control device(s) 230 to start, stop, increase, and/or decrease a flow of the therapeutic agent 238 from the therapeutic agent source 232 to the therapeutic agent delivery member 234.

In some implementations, locating the therapeutic agent source 232 in the handpiece 228 can beneficially provide for a relatively compact size of the delivery device 220 by, for example, reducing or eliminating relatively long external connections (e.g., tubes and/or cables) between the handpiece 228 and the therapeutic agent source 232. Whereas, in some implementations, locating the therapeutic agent source 232 in a housing that is separate from the handpiece 228 can, among other things, beneficially allow the therapeutic agent source 232 to store a relatively larger amount of the therapeutic agent 238 without impairing the handling capabilities of the handpiece 228.

Within examples, the delivery device 220 can provide for delivering the therapeutic agent 238 to a palatine canal and/or a pterygopalatine fossa of a patient. The boring element 236 is configured to form a passage in the palatine bone 102K between the nasal cavity and the palatine canal of the patient. In one example, the boring element 236 can include a needle that can pierce and penetrate through the palatine bone 102K. The boring element 236 can also include a needle actuator that can apply a force to the needle to cause the needle to penetrate through the palatine bone 102K.

In another example, the boring element 236 can apply a relatively high pressure stream of a boring fluid 242 to the palatine bone 102K to form the passage in the palatine bone 102K. In this example, the boring element 236 can be coupled (e.g., via the lumen(s) 240) to a boring fluid source 244, which contains the boring fluid 242 at the proximal portion 224. As an example, the boring fluid 242 can include water, saline, and/or the therapeutic agent 238. Thus, in an implementation in which the boring fluid 242 includes the therapeutic agent 238 the boring fluid source 244 can be the same as the therapeutic agent source 232.

As noted above, the delivery device 220 can include therapeutic agent delivery member 234 and/or the boring element 236. In some implementations, the delivery device 220 can be configured to form the passage through the palatine bone 102K and deliver the therapeutic agent to the palatine canal and/or the pterygopalatine fossa. In such implementations, the delivery device 220 can include the therapeutic agent source 232, the therapeutic agent delivery member 234, and the boring element 236.

However, in other implementations, the delivery device 220 can be implemented as two separate devices. For instance, the delivery device 220 can include a first device for forming the passage in the palatine bone 102K, and a second device that can be inserted into the passage and then deliver the therapeutic agent to the palatine canal and/or the pterygopalatine fossa. Thus, the first device can include a first handpiece, a first elongated shaft, the boring fluid source 244, and the boring element 236. Whereas, the second device can include a second handpiece, a second elongated shaft, the therapeutic agent source 232, and the therapeutic agent delivery member 234.

As shown in FIG. 2, the delivery device 220 can also include one or more stabilizer features 246 and/or one or more sensors 248. For instance, in some examples, the delivery device 220 can include the stabilizer features 246 to assist in retaining the delivery device 220 at a relatively fixed position while forming the passage in the palatine bone 102K and/or while delivering the therapeutic agent 238 to the target tissue. As described in further detail below, the stabilizer features 246 can include a suction device that can apply suction to a tissue in the nasal cavity and/or an expandable member (e.g., a balloon) that can expand engage tissue adjacent to the target tissue.

The sensor(s) 248 can facilitate positioning the delivery device 220 such that the distal portion 226 contacts a particular type of tissue and/or anatomical structure in the nasal cavity (e.g., a nasal cavity wall). For instance, the sensor(s) 248 can be located on the distal portion 226 of the delivery device 220. As examples, the sensor(s) 248 can include pressure sensors or load cells, temperature-sensitive elements, impedance monitoring elements, distance measurement sensors such as ultrasound-based or IR-based sensors, and/or other suitable sensor types.

In some implementations, the boring element 236 can additionally or alternatively be disabled unless the sensor(s) 248 indicate that the distal portion 226 is proximate to a tissue surface. For example, if the sensor(s) 248 do not indicate that the distal portion 226 is proximate to a tissue surface, a controller can prevent the boring element 236 from being activated and/or deployed by disabling the user control device(s) 230 associated with the boring element 236 (e.g. by locking out a spring mechanism that could be used to deploy the boring element 236, or by preventing the opening of a valve controlling the lumen 240 through which a high pressure fluid may travel). The controller can be implemented using hardware, software, and/or firmware. For example, controller can include one or more processors and a non-transitory computer readable medium (e.g., volatile and/or non-volatile memory) that stores machine language instructions or other executable instructions. The instructions, when executed by the one or more processors, may cause controller to carry out the various operations of the delivery device 220 described herein.

In this arrangement, the delivery device 220 can be used to perform a medical procedure on the target tissue in the nasal cavity. For example, in operation, the delivery device 220 can be inserted in the nasal cavity to position the distal portion 226 adjacent to the palatine bone 102K. After the distal portion 226 is positioned at the palatine bone 102K, the user control device(s) 230 can be operated to cause the boring element 236 to form the passage in the palatine bone 102K. For instance, the user control device(s) 230 can cause a needle to extend and/or move toward the palatine bone 102K to penetrate the palatine bone 102K. Additionally or alternatively, for instance, the user control device(s) 230 can cause the boring fluid source 244 to supply the boring fluid 242 to the boring element 236 (e.g., via the lumen(s) 240) and the boring element 236 can apply the boring fluid 242 to form the passage through the palatine bone 102K.

After forming the passage in the palatine bone 102K, the delivery device 220 can supply (e.g., via the lumen(s) 240) the therapeutic agent 238 from the therapeutic agent source 232 to the therapeutic agent delivery member 234. The therapeutic agent delivery member 234 can then deliver the therapeutic agent 238 through the passage to the palatine canal and/or the pterygopalatine fossa. In some implementations, the distal portion 226 can extend through the passage in the palatine bone 102K such that the therapeutic agent delivery member 234 is located in the palatine canal while delivering the therapeutic agent 238. In other implementations, the therapeutic agent delivery member 234 can deliver the therapeutic agent 238 to the passage and the therapeutic agent 238 can flow through the passage in the palatine bone 102K into the palatine canal.

Accordingly, in the arrangement shown in FIG. 2, the delivery device 220 can form a passage in the palatine bone 102K and apply the therapeutic agent 238 to palatine canal and/or pterygopalatine fossa to treat the target tissue. As described above, accessing and delivering the therapeutic agent 238 to the palatine canal and/or pterygopalatine fossa can enable a physician to have better control of pain and bleeding during surgical procedures in awake patients.

FIGS. 3A-15 show a plurality of distal portions that can be implemented in connection with the delivery device 200 shown in FIG. 2, according to examples of the present disclosure. In particular, FIGS. 3A-15 show various example implementations for the elongated shaft 222, the therapeutic agent delivery member 234, and/or the boring element 236 shown in FIG. 2. The examples shown in FIGS. 3A-15 will now be described.

Figure 3:
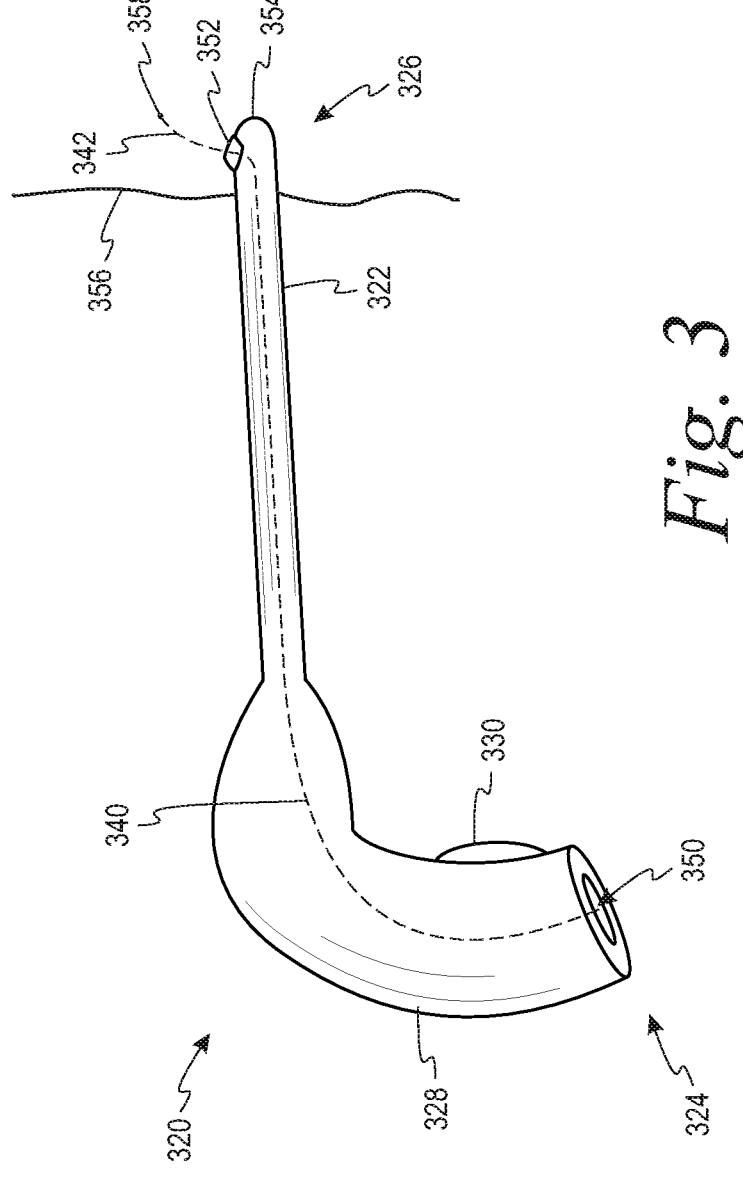
FIG. 3 shows a delivery device, according to an example.

FIG. 3 shows a delivery device 320 according to an example. As shown in FIG. 3, the delivery device 320 includes an elongated shaft 322 extending from a handpiece 328. The elongated shaft 322 can be flexible. This can help to navigate the elongated shaft 322 through the nasal cavity of a patient to a position proximate to the palatine bone 102K.

At a proximal portion 324 of the delivery device 320, the handpiece 328 includes an inflow port 350 which is configured to couple to, for example, an outflow nozzle of at least one of a canister of pressurized fluid, a canister of pressurized gas, or an external air compressor. The inflow port 350 is coupled to one or more output ports 352 at a distal portion 326 of the delivery device 320. More particularly, the delivery device 320 includes a lumen 340 that extends through the handpiece 328 and the elongated shaft 322 from the inflow port 350 to the output port(s) 352. In this example, the output port(s) 352 provide the boring element 236 and the therapeutic agent delivery member 234 described above with respect to FIG. 2.

As shown in FIG. 3, the user control device 330 is a trigger, which provides a release mechanism configured to cause a boring fluid 342 (e.g., water, saline, and/or a therapeutic agent) to be propelled through the lumen 340 in the elongated shaft 322 and exit the output port(s) 352 located proximate to a distal end 354 of the elongated shaft 322. When depressed, the user control device 330 activates a pressure gradient provided via the inflow port 350 to cause the boring fluid 342 to be driven as a fluid stream having a relatively high pressure out of the output port(s) 352. When the user control device 330 is released, the boring fluid 342 can cease to be outputted from output port(s) 352.

In general, when the user control device 330 is depressed (i.e., actuated), the fluid stream of the boring fluid 342 is suitable for forming a passage 358 in a relatively thin bony structure 356 (e.g., approximately 0.1 mm to approximately 3 mm) of the patient. For example, the output port(s) 352 can output the boring fluid 342 in the fluid stream with a diameter, a pressure, and/or a velocity that is suitable to bore a small hole into the palatine bone 102K to create the passage 358 through the palatine bone 102K to locations on an opposite side of the palatine bone 102K. As one example, the fluid stream of the boring fluid 342 can have a diameter of approximately 0.1 mm and a pressure between approximately 200 pounds per square inch (PSI) and approximately 5000 PSI. In some examples, the pressure, the velocity, and/or the diameter of the fluid stream of the boring fluid 342 can bore through the bony structure 356 over a time period of less than approximately 60 seconds.

In some examples, access to the palatine canal is achieved via the application of the boring fluid 342 to a mucosal wall in the nasal cavity in the region where the palatine bone 102K covers the palatine canal. After the hole in the bony structure 356 is created and the passage is established, the therapeutic agent (e.g., the therapeutic agent 238) can be delivered at a relatively lower pressure through the passage to the region of interest. In examples, a lower pressure for the therapeutic agent is provided by using a separate pressure source for the therapeutic agent (e.g., applying therapeutic agent by actuating a syringe and applying the boring fluid 342 with the assistance of a pressurized canister). In other examples, differing pressures for delivery of a boring fluid 342 and delivery of the therapeutic agent can be achieved by using a plurality of lumens 340 of different shape, length, and/or diameter.

As described above, within examples, the boring fluid 342 can be the same as the therapeutic agent or the boring fluid 342 can be different than the therapeutic agent. In implementations in which the boring fluid 342 is the same as the therapeutic agent, the delivery device 320 can adjust the pressure of the fluid stream at the output port(s) 352 to switch from a boring mode of operation to a therapeutic agent delivery mode of operation. In implementations in which the boring fluid 342 is different than the therapeutic agent, the lumen 240 can be decoupled from the boring fluid source 244 and coupled to the therapeutic agent source 232 to switch from a boring mode of operation to a therapeutic agent delivery mode of operation. In other implementations in which the boring fluid 342 is different than the therapeutic agent, more than one lumen 240 can be utilized.

Figure 4:
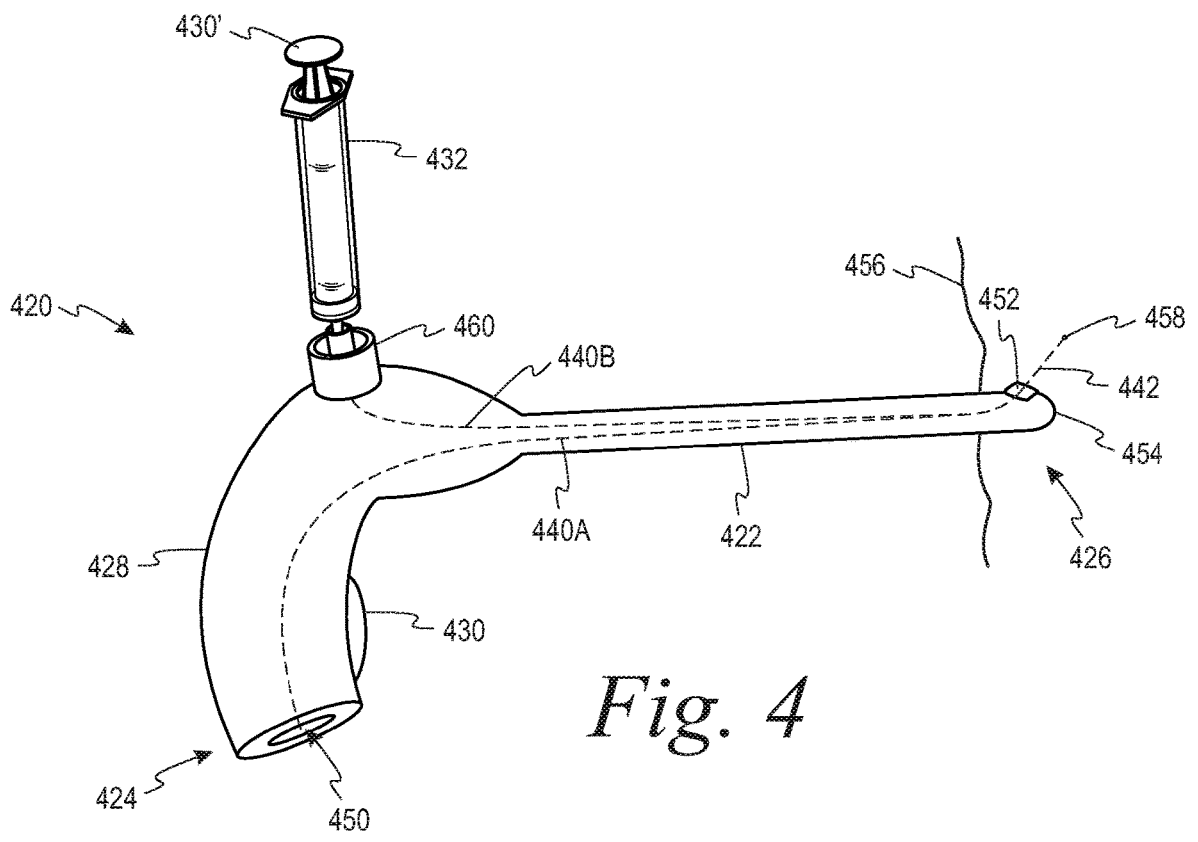
FIG. 4 shows a delivery device, according to another example.

Referring now to FIG. 4, a delivery device 420 is shown according to another example. As shown in FIG. 4, the delivery device 420 is substantially similar or identical to the delivery device 320 shown in FIG. 4, except the delivery device 420 includes a first lumen 440A for delivering a boring fluid 442 and a second lumen 440B for delivering the therapeutic agent (i.e., the delivery device 420 includes separate fluid-jet and substance delivery channels). Accordingly, the delivery device 420 can include a handpiece 428, an elongated shaft 440, an inflow port 450 at a proximal portion 424, one or more output ports 452 at a distal portion 426 (e.g., proximate to a distal end 454 of the elongated shaft 422), and/or a user control device 430 as described above.

In FIG. 4, the first lumen 440A couples the inflow port 450 to the output port(s) 452 and, thus, provides a conduit for supplying the boring fluid 442 to the output port(s) 452 responsive to the user actuating the user control device 430. As described above, the output port(s) 452 can output the boring fluid 442 as a fluid stream that can form a passage 458 in a bony structure 456 (e.g., the palatine bone 102K).

The second lumen 440B couples a therapeutic agent source 432 to the output port(s) 452 and, thus, provides a conduit for supplying the therapeutic agent to the output port(s) 452. In FIG. 4, the delivery device 420 includes a substance input port 460 on the handpiece 428. The substance input port 460 can couple the second lumen 440B to the therapeutic agent source 432. As an example, the substance input port 460 can be a luer type connection configured to interface with a medical syringe. In this arrangement, when a plunger 430' on the therapeutic agent source 432 is depressed, the therapeutic agent source 432 can supply the therapeutic agent to the output port(s) 452 via the second lumen 440B (i.e., the user control devices 230 in FIG. 2 can include the user control device 430 in the form of the trigger and the plunger 430').

Accordingly, as described above, the output port(s) 452 can provide the boring element 236 and the therapeutic agent delivery member 234 shown in FIG. 2. In some implementations, the output port(s) 452 can include a plurality of output ports 452 including a first output port 452 coupled to the first lumen 440A and a second output port 452 coupled to the second lumen 440B. In other implementations, each output port 452 can be coupled to both the first lumen 440A and the second lumen 440B. For instance, in one example, the delivery device 420 can include a valve coupled to the user control device 430. The valve can be configured such that (i) the valve couples the output port(s) 452 to the first lumen 440A when the user control device 430 is actuated (e.g., depressed), and (ii) the valve couples the output port(s) 452 to the second lumen 440B when the user control device 430 is not actuated (e.g., in a resting state).

Within examples, a method of operating the delivery device 420 can include the following steps: (1) positioning the delivery device 420 such that the distal portion 426 is proximal to a tissue or bony region where it is desired to bore a small hole to gain access to the opposite side of this tissue or bony region; (2) depressing the user control device 430 to force a high-pressure fluid jet out of the output port(s) 452 (i.e., the boring element 236), creating a small hole in the bone or tissue region; (3) releasing the user control device 430, allowing the user control device 430 to return to the resting state and thereby causing the valve in the delivery device 420 to couple the output port(s) 452 to the second lumen 440B originating from the substance input port 460; (4) applying the therapeutic agent via the output port(s) 452 (i.e., the therapeutic agent delivery member 234) through the passage 458 or in a general vicinity of the passage 458 at a relatively low output pressure (e.g., by deploying a plunger on a syringe connected to substance input port 460).

In FIGS. 3-4, the boring element 236 of the delivery device 320, 420 is configured to deliver a fluid stream of the boring fluid 242, 342, 442 to form the passage 358, 458 in the bony structure (e.g., the palatine bone 102K). However, as described above, the boring element 236 can additionally or alternatively include one or more needles for forming the passage in other examples.

Accordingly, within examples, the palatine canal can be accessed directly by using a needle or a plurality of needles to penetrate the palatine bone 102K. In some implementations, the needle(s) can be dynamic and selectively deployed only when the needle(s) are positioned in place, eliminating discomfort associated with incidental interactions between sharp edges of the needle(s) and nasal cavity tissues. After deployment, the needle(s) can penetrate the palatine bone 102K and, in some instance, can further penetrate surrounding tissues to establish a passage to the palatine canal.

In some implementations, the therapeutic agent 238 can be delivered through a lumen in the needle(s) while maintaining the needle(s) in position through the palatine bone 102K. In other implementations, the needle(s) can be retracted or otherwise removed, leaving the passage through which the therapeutic agent 238 can be delivered. In such implementations, a second device (e.g., a cannula or similar delivery vessel) can be deployed as part of the needle(s) removal process in order to maintain the patency of the passage created through the palatine bone 102K.

Figure 5A:
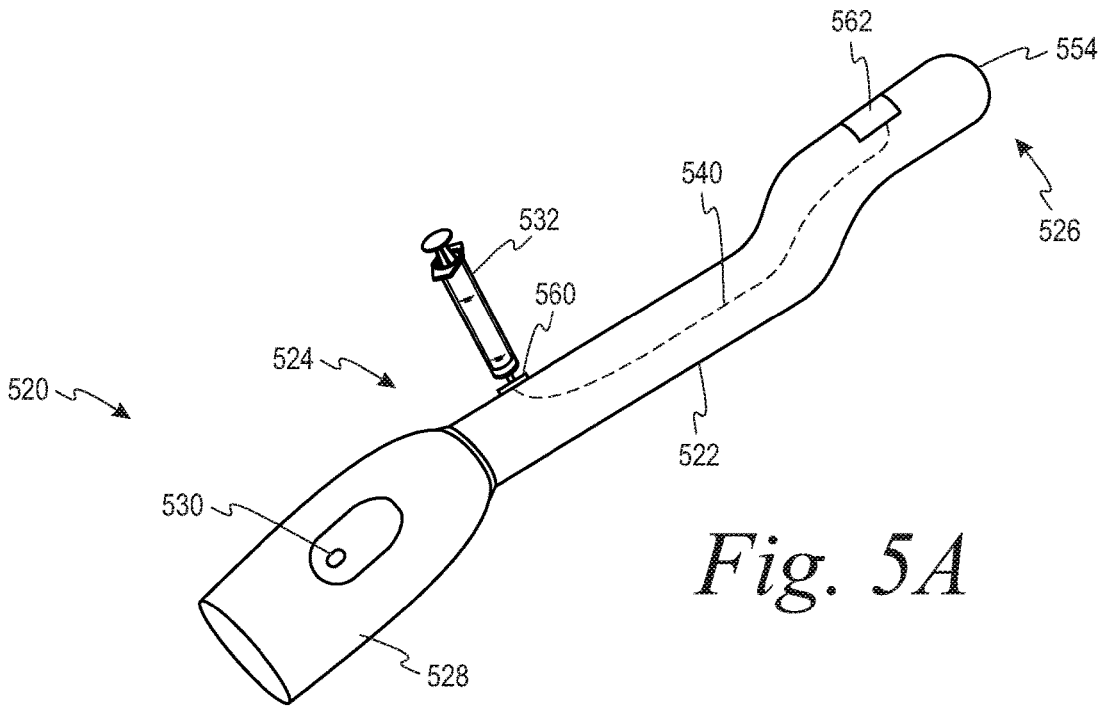
FIG. 5 shows a delivery device, according to another example.

Referring now to FIGS. 5A-5C, a delivery device 520 that can utilize a needle to puncture the palatine bone 102K to access the palatine canal is shown according to another example. As shown in FIG. 5A, the delivery device 520 can include a handpiece 528, an elongated shaft 522, a lumen 540 in the elongated shaft 522, a substance input port 560 coupled to a first end of the lumen 540, and an therapeutic agent source 532 that can couple to the substance input port 560 as described above.

Additionally, as shown in FIGS. 5A-5C, a distal portion 526 of the delivery device 520 can include a compartment 562 and a needle 564. In FIGS. 5A-5C, the compartment 562 and the needle 564 are proximate to a distal end 554 of the elongated shaft 522. However, the compartment 562 and the needle 564 can be in other locations in other examples.

As described above, the needle 564 can puncture a bony structure such as the palatine bone 102K to form a passage through the bony structure. Accordingly, the needle 564 in FIGS. 5A-5C can provide the boring element 236 shown in FIG. 2. In examples, the needle 564 can be made of a lightweight material with a relatively strong tensile strength (e.g., titanium). Also, in examples, the needle 564 can have a length of approximately 0.5 mm to approximately 5 mm.

As also described above, the boring element 236 can also include a needle actuator that can apply a force to the needle 564 to cause the needle 564 to penetrate through the bony structure (e.g., the palatine bone 102K). In FIGS. 5B-5C, the needle actuator is an expandable member 566 (e.g., a balloon) that is coupled to the needle 564. As examples, the expandable member 566 can be a relatively thin, compliant structure comprised of a material resistant to tear (e.g., latex, nitrile, and/or neoprene). In one example, the expandable member 566 can be made from a material having a thickness that is less than approximately 1 mm thick. In another example, the expandable member 566 can be made from a material having a thickness that is less than approximately 0.25 mm. More generally, the expandable member 566 can be configured for high-pressure, high-velocity rapid inflation without suffering a material failure, tear, or being detached from the elongated shaft 522 of the delivery device 520.

FIG. 5B depicts the expandable member 566 in a deflated state, and FIG. 5C depicts the expandable member 566 in an inflated state. As shown in FIG. 5B, when the expandable member 566 is in the deflated state, the expandable member 566 and the needle 564 can be recessed within the compartment 562. This can beneficially provide the distal portion 526 of the delivery device 520 with a relatively small profile (e.g., size and shape) such that inserting the delivery device 520 in the nasal cavity can be atraumatic.

In this example, the user control device 530 (e.g., a button) on the handpiece 528 can be actuated to transition the expandable member 566 from the deflated state to the inflated state. For instance, depressing a trigger of the user control device 360 can cause a rapid expansion of the expandable member 566, which orients the needle 564 approximately normal to the elongated shaft 522 at the distal portion 526 and forces the needle 564 through the palatine bone 102K 556 so that at least a tip of the needle 564 is in a region of the palatine canal 568.

After the needle 564 has punctured the palatine bone 102K 556 and created a passage into the palatine canal 568, the delivery device 520 can deliver the therapeutic agent to the palatine canal 568. In one example, the needle 564 can include the lumen 540 that is coupled to the therapeutic agent source 532 such that the therapeutic agent can be delivered via an output port 552 in the needle 564. In another example, a second device can be used to deliver the therapeutic agent via the passage in the palatine bone 102K formed by the needle 564.

Referring now to FIGS. 6A-6C, a delivery device 620 including a needle 664 for forming the passage in the palatine bone 102K is shown according to another example. As shown in FIGS. 6A-6C, the delivery device 620 includes a handpiece 628, an inflow port 650 in the handpiece 628 at a proximal portion 624 of the delivery device 620, an elongated shaft 622 extending from the handpiece 628, a lumen 640 in the handpiece 628 and the elongated shaft 622, a user control device 630, a compartment 662 in the elongated shaft 622 at a distal portion 626 of the delivery device 620, and a needle 664 in the compartment 662, as described above.

In FIGS. 6A-6C, the needle actuator is a spring 666 that can force the needle 664 from a retracted position shown in FIG. 6B to an extended position shown in FIG. 6C. For example, in FIG. 6B, the spring 666 is in an initial compressed state with the needle 664 in the lumen 640 and the compartment 662 such that the needle 664 is not exposed. This can beneficially provide the distal portion 626 of the delivery device 620 with a relatively small profile (e.g., size and shape) such that inserting the delivery device 620 in the nasal cavity can be atraumatic When a distal end 654 of the elongated shaft 622 is located adjacent to a tissue region and/or bony region desired to penetrate, the operator can actuate the user control device 630 on the handpiece 628 to release the spring 666 from the initial compressed state and force the needle 664 out of the lumen 640 to penetrate a thin bone such as a the palatine bone 102K. In an example, the user control device 630 can be a button that may be depressed by the operator to cause the spring 666 to force the needle 664 out of the lumen 640 and the compartment 662. Within examples, the spring 666 can be comprised of stainless steel, brass, or another suitable material. The spring 666 can have a spring constant such that the spring 666 can apply a force to the needle 664 that is suitable for forcing the needle 664 through the bony structure (e.g., the palatine bone 102K).

In examples, the delivery device 620 can also include one or more contact sensors 670 proximate to a location of the needle 664 to facilitate placement of the delivery device 620 such that the distal end 654 is in contact with the nasal cavity wall. As examples, the contact sensors 670 can include one or more pressure sensors, load cells, temperature-sensitive elements, impedance monitoring elements, and/or distance measurement sensors (e.g., ultrasound-based distance measurement sensors or IR-based distance measurement sensors). In some implementations, the user control device 630 can be disabled unless contact sensors 670 indicate proximity to a tissue surface. This can help to reduce (or prevent) the operator from prematurely actuating user control device 630 and extending the needle 664 into an unintended tissue region.

In one implementation, a controller can be coupled to the user control device 630 and the contact sensors 670. When the user control device 630 is actuated, the user control device 630 can provide a signal to the controller. Similarly, when the contact sensors 670 detect a predetermined proximity to the tissue surface, the contact sensors 670 can provide a signal to the controller. The controller can be configured such that (i) the controller releases the spring 666 when the controller receives the signal from the user control device 630 and the signal from the contact sensors 670, and (ii) the controller does not release the spring 666 when the controller receives only one of the signals or none of the signals from the user control device 630 and the contact sensors 670. In one example, the controller can send a signal to a motor to move a latch and thereby release the spring 666.

After the needle 664 forms the passage through the bony structure, the delivery device 620 can deliver a therapeutic agent to a region of interest (e.g., the palatine canal) via the inflow port 650, the lumen 640, and an output port 652, as described above. Within examples, the delivery device 620 can also include a mechanism to retract needle 664 after forming the passage and/or delivering the therapeutic agent through the passage. For example, the delivery device 620 can include a mechanical dial, which when engaged and rotated can pull the spring 666 back into the elongated shaft 622. Retracting the needle 664 can facilitate removing the delivery device 620 from the nasal cavity without causing unwanted collateral tissue damage during removal.

Within examples, the needle 564, 664 can include a bio-absorbable material (e.g., a bioresorbable material) such as, for instance, sugar-based compounds and/or synthetic polymers (e.g., polyglycolic acid (PGA) or polylactic acid (PLA)). The bio-absorbable material of the needle 564, 664 can be absorbed over a relatively short period of time or degrade relatively slowly (e.g., over a year or more). For instance, in some implementations, the needle 564, 664 can be completely resorbed in a matter of weeks, and, in other implementations, the needle 564, 664 can be completely resorbed in a matter of hours (e.g., less than one day). In examples in which the needle 564, 664 is made from a bio-absorbable material, the needle 564, 664 can initially have a tensile strength comparable to stainless steel or similar materials used for puncturing rigid tissues.

In some examples, the degradation of the needle 564, 664 made from the bio-absorbable material can be accelerated to limit an amount of time for which the passage exists through the tissue and/or the bony structure. This can be accomplished, for example, by exposing the needle 564, 664 to a substance, a temperature, or other environmental factor that causes the needle 564, 664 to rapidly dissolve. For example, the needle 564, 664 can have a greater mechanical integrity when it is dry and located in the elongated shaft 522, 622 prior to deployment (i.e., as compared to after the needle 564, 664 is deployed to puncture the bony structure). In some examples, delivering the therapeutic agent through the needle 564, 664 can initiate and/or accelerate breaking down the needle 564, 664, allowing the passage through the bony structure to close.

As described above, in some examples, the delivery device 220, 320, 420, 520, 620 can include the stabilization feature 246 to assist in retaining the delivery device 220, 320, 420, 520, 620 at a relatively fixed position while forming the passage in the palatine bone 102K and/or while delivering the therapeutic agent 238 to the target tissue. The stabilization feature 246 can thus help to mitigate a possibility that a contact force of the fluid stream of boring fluid 242 342, 442 and/or the needle 564, 664 on the palatine bone 102K may cause the delivery device 220, 320, 420, 520, 620 to be pushed away from the palatine bone 102K after initial contact with the hard bone surface (i.e., without penetrating the palatine bone 102K).

In one example, the stabilization feature 246 can include one or more suction port(s) at the distal portion 226, 326, 426, 526, 626 of the delivery device 220, 320, 420, 520, 620 (e.g., near the distal end 354, 454, 554, 654 of the elongated shaft 222, 322, 422, 522, 622 proximate to the output port(s) 352, 452 and/or the needle 564, 664). The suction port(s) can be coupled to a negative pressure source (e.g., a vacuum source) at the proximal portion 224 via at least one of the lumen(s) 240. The negative pressure source can be operable by the user control device(s) 230 to apply suction at the suction port(s) via the lumen(s) 240. In operation, the suction port(s) can engage a tissue adjacent to a site at which the passage is to be formed. When the negative pressure source is activated (e.g., by opening a valve), the negative pressure can draw the suction port(s) and adjacent tissues into close contact and maintain this contact with a force that is proportional to a strength of the vacuum applied. As such, the negative pressure source and the vacuum port(s) can provide a force that holds and stabilizes the distal portion 226, 326, 426, 526, 626 of the delivery device 220, 320, 420, 520, 620 close to the palatine bone 102K to facilitate the fluid stream of boring fluid 242 342, 442 and/or the needle 564, 664 penetrating the palatine bone 102K.

In another example, the stabilization feature 246 can additionally or alternatively include a balloon. FIGS. 7A-7B show a delivery device 720 that includes an expandable member 772 (e.g., a balloon) as the stabilization feature 246. As shown in FIGS. 7A-7B, the delivery device 720 includes an elongated shaft 722 having a distal end 754. The delivery device 720 also includes a boring element 736 on a first side of the elongated shaft 722, and the balloon on a second side of the elongated shaft 722. The second side can be opposite of the first side. The boring element 736 can be configured to form a passage via a fluid stream of the boring fluid 242 and/or a needle 564, 664 as described above.

In FIG. 7A, the distal end 754 of the elongated shaft 722 is positioned such that the boring element 736 is adjacent to a lateral wall of the nasal cavity 700 proximate to the palatine bone 702K in a region where the palatine bone 702K covers the palatine canal 702R. After the delivery device 720 is positioned adjacent to the lateral wall of the nasal cavity as shown in FIG. 7A, at least one of the user control device(s) 230 shown in FIG. 2 can be actuated to inflate the expandable member 772. As shown in FIG. 7B, when the expandable member 772 is inflated, the expandable member 772 can establish contact with a medial wall 774 of the nasal cavity 700 or other nearby structures. Within examples, the expandable member 772 can be inflated to a pressure such that the expandable member 772 is rigid and resistant to compression and thereby applies a stabilization force against opposing tissues, holding the delivery device 720 in place as the boring element 736 forms the passage in the palatine bone 702K. After the passage in the palatine bone 702K is formed, the expandable member 772 can be deflated to facilitate removal of the delivery device 720 from the nasal cavity.

Figure 1B:
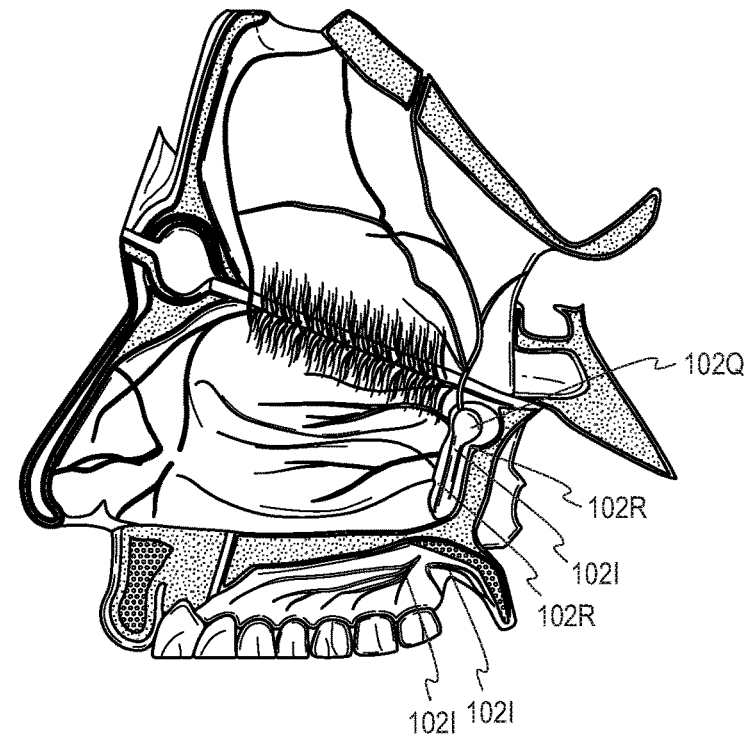
FIG. 1B shows anatomical structures in the nasal cavity and mouth.
Figure 1C:
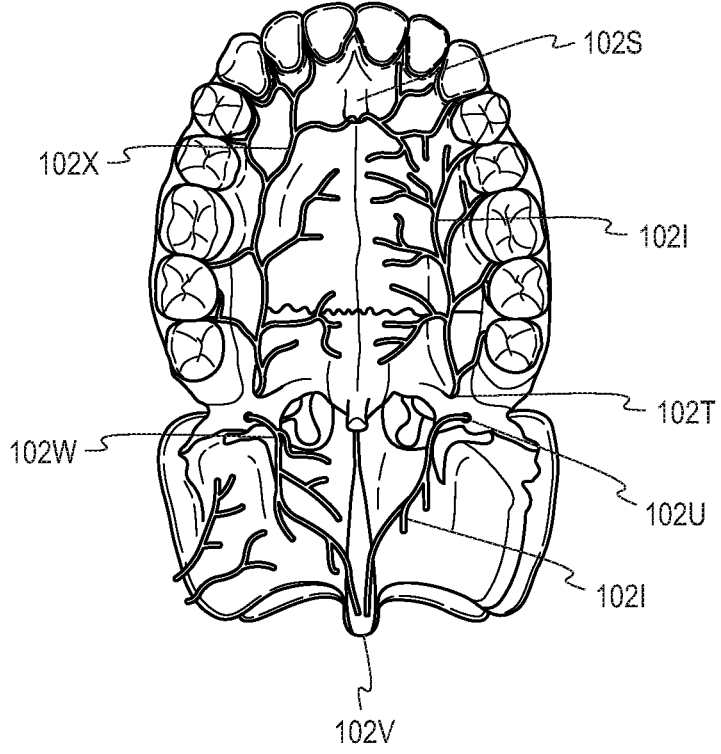
FIG. 1C shows anatomical structures in the nasal cavity and mouth.

In some implementations, an advantageous (or an optimal) location to create the passage for access to a region may not be the same location where it is desired to deliver the therapeutic agent. For example, access to a region such as the palatine canal 102R (shown in FIG. 1B) may be most easily accomplished at a region where the palatine bone 102K is thinnest, in the region where tool access is least limited by the irregular shape of the nasal cavity 100, and/or a balance between these and other factors. This optimal access region may not directly coincide with the location of the nerves within the palatine canal 102R or the sphenopalatine ganglion. Depending on the orientation of the anatomy (e.g., in nasal cavity procedures) and/or the position/angle of the subject's head, gravity may cause the therapeutic agent to naturally move away from the introduction site and towards desired regions. In other scenarios, gravity may cause the therapeutic agent to naturally move away from the introduction site and away from desired regions. In examples, the delivery velocity, and therapeutic agent density, thickness, and surface adhesion may be configured to limit the effects of gravity causing the therapeutic agent to move away from a targeted treatment site.

Figure 8:
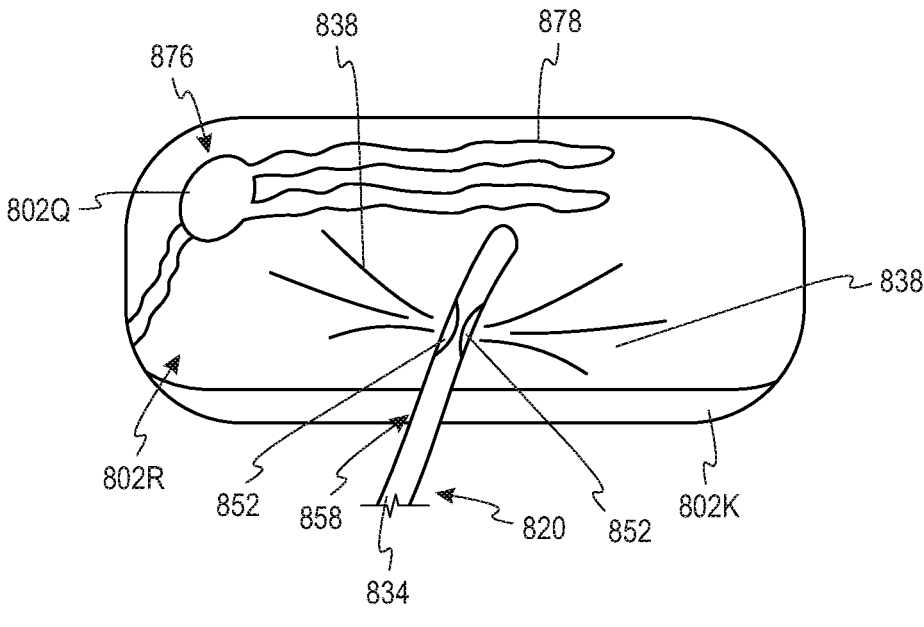
FIG. 8 shows a delivery device, according to another example.

As described above, the delivery device 220, 320, 420, 520, 620, 720 can deliver the therapeutic agent 238 to a target tissue via the passage formed in the bony structure (e.g., the palatine bone 102K). FIG. 8 depicts a delivery device 820 applying a therapeutic agent 838 to a target tissue 876, according to one example. As shown in FIG. 8, the delivery device 820 includes a delivery conduit 834 extending through a passage 858 in a palatine bone 802K and into a palatine canal 802R. Within examples, the delivery conduit 834 can be a distal end of an elongated shaft of the delivery device 820 and/or a needle (e.g., the needle 564, 664 in FIGS. 5A-6C).

In FIG. 8, the target tissue 876 includes a plurality of nerves 878 and a nerve ganglion 802Q. Within examples, the therapeutic agent 838 can be directly applied to the nerves 878 and/or the therapeutic agent 838 can be directly applied to the nerve ganglion 802Q. As shown in FIG. 8, the delivery conduit 834 can include one or more output ports 852 that can eject the therapeutic agent 838 along one or more directions that are transverse (e.g., approximately orthogonal) to a longitudinal axis of the delivery conduit 834. This can facilitate the therapeutic agent 838 reaching anatomical targets that are off-axis relative to the orientation of the passage 858 and/or the delivery conduit 834.

Within examples, the delivery device 820 can include the delivery conduit 834 and a boring element, or the delivery device 820 can be a second device that includes only the delivery conduit 834 and omits the boring element.

Figure 9:
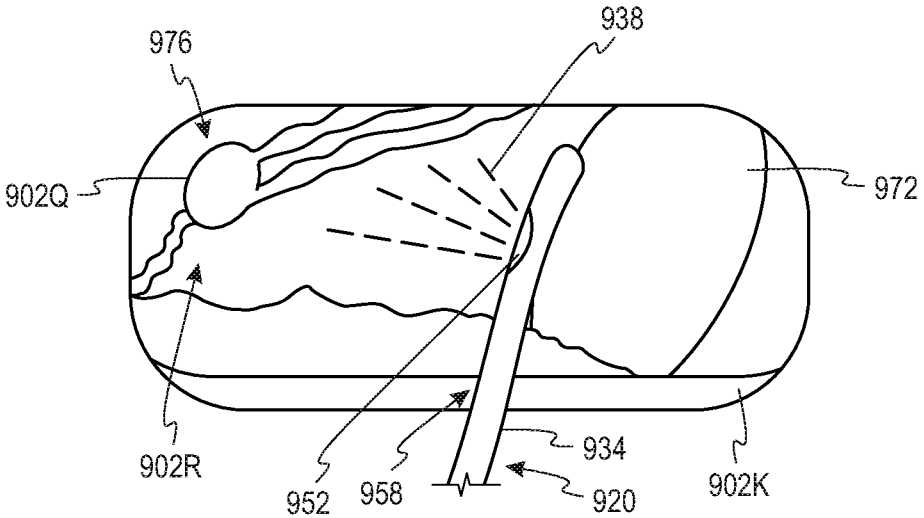
FIG. 9 shows a delivery device, according to another example.

FIG. 9 depicts a delivery device 920 applying a therapeutic agent 938 to a target tissue 976, according to another example. As shown in FIG. 9, the delivery device 920 includes a delivery conduit 934 extending through a passage 958 in a palatine bone 902K and into a palatine canal 902R. Within examples, the delivery conduit 934 can be a distal end of an elongated shaft of the delivery device 920 and/or a needle (e.g., the needle 564, 664 in FIGS. 5A-6C).

As shown in FIG. 9, the delivery conduit 934 includes an output port 952 on a first side and a balloon 972 on a second side, which can oppose the first side. In this example, the delivery conduit 934 is inserted in the passage 958 with the balloon 972 initially in a deflated state allowing the delivery conduit 934 to have a slim profile capable of traversing a relatively small size of the passage 958 (e.g., a diameter less than approximately 1 mm). Once positioned through the passage 958 into the palatine canal 902R, the balloon 972 can be inflated using an inflation mechanism (e.g., a pump/valve system that is proximate to a handpiece of the delivery device 920).

As an example, the balloon 972 can be a compliant material (e.g., latex) that can contact tissue walls and effectively seal off a portion of the palatine canal 902R. Accordingly, as the therapeutic agent 938 is ejected from the output port 952, the balloon 972 can cause the therapeutic agent 938 to collect and remain in a space limited by the balloon 972. This region where the therapeutic agent 938 collects can include a ganglion 902Q. After completing delivery of the therapeutic agent 938, the balloon 972 can be deflated (e.g., by releasing a valve at the handpiece), and the delivery conduit 934 can be removed from the passage 958.

In some examples, the delivery conduit 934 can remove excess therapeutic agent 938 that has gathered in the tissue region prior to deflating the balloon 972. For example, after completing delivery of the therapeutic agent 938, a negative pressure gradient can be applied to the delivery conduit 934, forcing excess therapeutic agent 938 that has accumulated in the treatment region to be sucked back into the delivery conduit 934 and removed from the treatment region. In an alternative example, the delivery device 920 can include a separate fluid removal lumen that is configured to be coupled to a negative/pressure vacuum source.

In some examples, the delivery device 220, 320, 420, 520, 620, 720, 820, 920 can operate the boring element 236 (e.g., using a fluid stream of the boring fluid and/or a needle) based on information provided by a location guidance system. For instance, one or more images provided by an endoscope can allow for visualization of tissue surfaces and of anatomical landmarks, which can guide procedures, but may not allow for direct visualization of anatomy deeper than surface tissues. For example, when attempting to access the palatine canal 102R through the palatine bone 102K, endoscopic guidance can be used to identify landmarks such as the turbinate bones and sphenopalatine foramen 102G to use as guidance for where to puncture the palatine bone 102K, but increased confidence may be achieved and user errors decreased via mechanisms that identify the location of the palatine canal 102R directly.

Within examples, the delivery device 220, 320, 420, 520, 620, 720, 820, 920 can include an ultrasound, infrared, laser, impedance, or other type of sensor on the distal end 354, 454, 554, 654, 754 of the elongated shaft 222, 322, 422, 522, 622, 722 proximate to the boring element 236. For instance, an infrared sensor can be provided at the distal end 354, 454, 554, 654, 754 such that the infrared sensor can identify a presence of a cavity such as the palatine canal 102R. Identification can be automatic and information can be conveyed to the user via an optical, auditory, or mechanical device. For example, a colored indicator can illuminate when the boring element 236 is located in a tissue region adjacent to the palatine canal 102R.

Within examples, the sensors can be included to assist with determining a desirable (e.g., an optimal) penetration site. For example, laser, ultrasound, or other types of sensors can be utilized to scan locally within a confined region to determine an area where a bone is thinnest. The thin area of bone wall can allow for a simple access point that can be penetrated with less force and/or at a higher success rate relative to thicker areas of bone. In examples, an ultrasound transducer operating at a 10-15 MHz transmit frequency may be affixed to the distal end 354, 454, 554, 654, 754 of the elongated shaft 222, 322, 422, 522, 622, 722 proximate to the location of the boring element 236. In an implementation, the ultrasound transducer can be configured to produce A-mode scans and port data to electronics in the handpiece 228. Additionally, for instance, the delivery device 220, 320, 420, 520, 620, 720, 820, 920 can include a non-transitory computer readable media storing instructions that when executed by a processor provide for implementing algorithms to assess a property of the A-mode scans that can be used to determine a wall thickness (e.g., edge detection algorithms that can be used to determine a leading edge and a trailing edges of a strong reflector such as a bony structure and/or signal loss assessment algorithms that can determine how much power an ultrasound signal has lost due to the presence of a highly-attenuating bony medium).

In some implementations, it may be desirable to close the passage in the bony structure (e.g., the palatine bone 102K) after delivering the therapeutic agent 238 to the target tissue. For instance, in some examples, the delivery device 220, 320, 420, 520, 620, 720, 820, 920 can deliver the therapeutic agent 238 over a period of time that can be substantially shorter than a period of time over which the passage can naturally close. Within examples, a device can be configured to close or otherwise fill a space that remains after the creation of a passage.

In an example, a nasal tool can be configured to deliver a cap that can be positioned so as to interface with a passage through a tissue or bony structure in such a way that the cap seals the hole that has been created. The cap can be mushroom-shaped with a smooth top that is low profile and with soft edges so as to not be irritating to nasal tissue or restrict airflow in the nasal passage. A diameter of the top portion of the cap can be larger than a diameter of the hole in the tissue and/or bony structure so as to completely seal the hole. In some examples, a stem extending from the cap can have an outer diameter that is slightly less than a diameter of the passage such that when the cap is inserted into the hole a friction force keeps the cap in place.

FIGS. 10A-10B depict a cap 1080 sealing a passage 1058 through tissue and/or a bony structure (e.g., a palatine bone 1002K) according to an example. More particularly, FIG. 10A depicts the cap 1080 in a retracted state and FIG. 10B depicts the cap 1080 in an expanded state. As shown in FIGS. 10A-10B, the cap 1080 can include a top portion 1082 and a stem 1084 extending from the top portion 1082. The top portion 1082 can have a diameter that is greater than a diameter of the passage 1058 such that the top portion 1082 can entirely cover a hole in the palatine bone 1002K. The stem 1084 can have a diameter that is adjustable. The adjustability of the diameter of the stem 1084 can facilitate placing the cap 1080 in the passage 1058 and provide sufficient radial outward force to maintain the cap 1080 in a fixed position.

In operation, a nasal tool can be used to deliver the cap 1080, with or without guidance such as endoscopic visualization, to the hole associated with the passage 1058. Within examples, the delivery device 1020 can include an endoscopic visualization system such as the system disclosed in U.S. Publ. No. 2018/0153375, the contents of which is hereby incorporated by reference in its entirety. As shown in FIG. 10A, the stem 1084 can have a relatively small diameter that is smaller than a diameter of the passage 1058 to facilitate easy placement of the cap 1080 in the passage 1058 when the cap 1080 is in the retracted state. After the stem 1084 is positioned in the passage 1058, the nasal tool can perform an action on the top portion 1082 to cause the diameter of the stem 1084 to expand to the expanded state shown in FIG. 10B. As shown in FIG. 10B, in the expanded state, the cap 1080 can have a diameter that is approximately equal to diameter of the passage 1058, providing a friction force and/or radial outward force that maintains the cap 1080 firmly in a fixed position.

In one example, the surgical tool can twist and/or rotate the top portion 1082 to move a screw 1086 or other internal component deeper into an interior of stem 1084, which causes an anchor 1088 to splay outward, increasing the diameter of at least a portion of stem 1084. In some examples, the cap 1080 can be composed of a bio-absorbable material that slowly degrades over time, allowing the passage to close naturally.

FIG. 11 shows a nasal tool 1190 containing an introducer sheath 1192 that compresses a plug 1194. The plug 1194 can be expandable. The introducer sheath 1192 can be translatable from a first position in which the introducer sheath 1192 covers the plug 1194 to a second position in which the introducer sheath 1192 exposes the plug 1194. When the introducer sheath 1192 is in the first position, the introducer sheath 1192 and the plug 1194 can have a diameter that is smaller than a diameter of a passage 1158 in a bony structure (e.g., a palatine bone 1102K). This can facilitate inserting the introducer sheath 1192 and the plug 1194 in the passage 1158.

After inserting the introducer sheath 1192 and the plug 1194 in the passage 1158, the introducer sheath 1192 can be withdrawn from the first position to the second position to expose the plug 1194. Responsive to exposing the plug 1194, the plug 1194 can expand from a first size to a second size to fill the passage 1158. In some implementations, after the plug 1194 fills the passage 1158, the plug 1194 can be decoupled from the nasal tool 1090 and left in place in the passage 1158.

In some examples, the plug 1194 can be comprised of a soft, non-irritating material such as a foam. The plug 1194 can additionally or alternatively be comprised of one or more bio-absorbable materials that will naturally degrade over time, allowing the passage 1158 to close naturally. The plug 1194 can be coated with or otherwise adapted to elute a therapeutic agent such as an antibiotic or steroid or another agent that may assist with wound healing, infection control, or other purposes.

In examples, access the palatine canal 102R and pterygopalatine fossa to apply anesthesia or another therapeutic agent to the nerves and/or blood vessels within the palatine canal 102R may be performed without penetration of a bone. For example, a transmucosal injection or a natural opening such as a foramen, for example the sphenopalatine foramen 102G (shown in FIG. 1A) or the greater palatine foramen 102T, may be used to access the palatine canal 102R. In an implementation in which a transmucosal injection is used, the transmucosal injection can create a bleb and from there fluid can migrate to the foramen or microforamina. Within examples, delivery devices and methods used to access natural orifices can be configured to prevent accidental injection of a therapeutic agent 238 into an artery, which could pose a serious risk to the subject.

Figure 12:
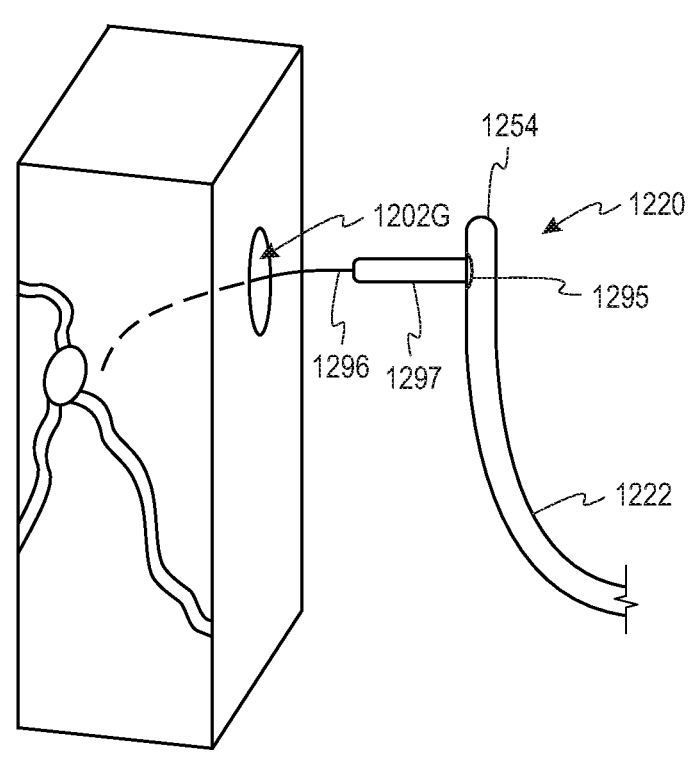
FIG. 12 shows a delivery device, according to another example.

FIG. 12 shows a delivery device 1220 according to another example. As shown in FIG. 12, the delivery device 1220 includes an elongated shaft 1222 and a deployment port 1295 proximate to a distal end 1254 of the elongated shaft 1222. The deployment port 1295 can provide an aperture through which a guidewire 1296 can extend. For instance, the guidewire 1296 can be actuated by at least one of the user control device(s) 230 shown in FIG. 2 (e.g., a dial on or near the handpiece 228) to extend or retract the guidewire 1296 relative to the elongated shaft 1222.

In an example, the guidewire 1296 can be thin (e.g., having a diameter that is less than approximately 0.04 inches and/or less than approximately 0.02 inches) and be comprised of a material (e.g., stainless steel) that (i) provides for some degree of flexibility and (ii) also provides a mechanical rigidity that is suitable for the guidewire 1296 to be manipulated and moved by user (e.g., using the user control device 230 at the handpiece 228). In one implementation, the guidewire 1296 can be manufactured such that it has a rounded end that represents a blunt surface. This can help to mitigate (or prevent) the guidewire 1296 from piercing any tissue structures. Also, in some examples, the guidewire 1296 can be coated with a substance such as a polymer or lacquer to further reduce the risk of tissue damage arising from incidental contact.

Under endoscopic guidance or another suitable guiding mechanism, the deployment port 1295 can be positioned proximate to a sphenopalatine foramen 1202G and the guidewire 1296 can be extended and manipulated (e.g., by adjusting a dial on the handpiece 228) such that the guidewire 1296 enters the sphenopalatine foramen 1202G. With the guidewire 1296 in place, a delivery conduit 1297 (e.g., a tube) may be extended over the guidewire 1296 such that the delivery conduit 1297 enters the sphenopalatine foramen 1202G (e.g., by manipulating another user control device 230 on the handpiece 228 such as, for instance, by pressing a button or moving a slider along a tract in the handpiece 228). The delivery conduit 1297 can be made from a relatively soft and a relatively flexible material. For instance, the delivery conduit 1297 can be comprised of silicone or another material with mechanical properties that reduces (or minimizes) a risk of tissue damage from incidental contact but also allows for a therapeutic agent to be delivered through a lumen in the delivery conduit 1297 with reasonable pressure (e.g., a pressure that may be created by depressing the plunger on a standard medical syringe).

With the delivery conduit 1297 in the sphenopalatine foramen 1202G, the guidewire 1296 may be retracted and the therapeutic agent can be delivered through the delivery conduit 1297 into the anatomical region on the distal side of the sphenopalatine foramen 1202G. This allows for the benefits of using a soft, safe material to deliver the therapeutic agent to a sensitive area while allowing for the mechanical dexterity and manipulability of more rigid materials.

In FIG. 12, the delivery device 1220 is described in the context of delivering the therapeutic agent through the sphenopalatine foramen 1202G according to an example. However, in other examples, the delivery device can enter the palatine canal 1302R via the greater palatine foramen 1302T as shown in FIGS. 13A-13B.

Figure 13A:
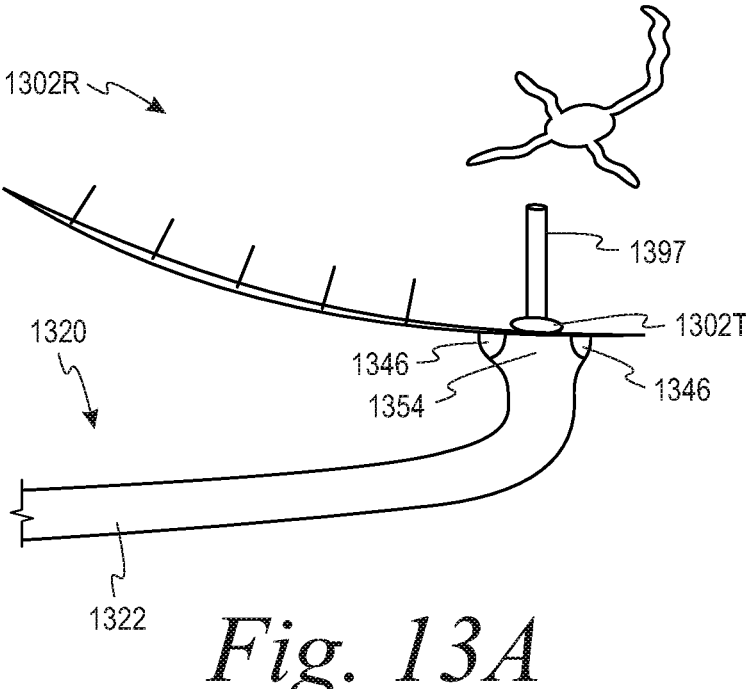
FIG. 13A shows a delivery device, according to another example.

FIG. 13A shows a delivery device 1320 according to another example. As shown in FIG. 13A, the delivery device 1320 includes an elongated shaft 1322. In one implementation, the delivery device 1320 can enter a subject's mouth and extend posteriorly toward the molars. The elongated shaft 1322 of the delivery device 1320 can include an angled distal end 1354, which is adapted to aim superiorly toward a soft palate or hard palate.

FIG. 13B shows the distal end 1354 of the elongated shaft 1322. As shown in FIG. 13B, the distal end 1354 can be circular with a diameter sufficiently large (e.g., approximately 0.5 inches) such that the distal end 1354 can circumscribe the greater palatine foramen 1302T. Using a manual palpation, endoscopic guidance, or another suitable visualization or location technique, an operator can manipulate delivery device 1320 such that the distal end 1354 is positioned to surround the greater palatine foramen 1302T.

In some examples, the distal end 1354 can apply a relatively mild suction via one or more suction ports 1346 that are connected to one or more lumen(s) in the elongated shaft 1322 that interface with a negative pressure or vacuum source in the region of the handpiece as described above. In other examples, the delivery device 1320 can additionally or alternatively include another stabilization feature such as, for instance, one or more deployable anchors to help maintain a position of the distal end 1354 over the greater palatine foramen 1302T.

While the distal end 1354 is positioned over the greater palatine foramen 1302T, the operator can operate a user control device to cause a delivery conduit 1397 (e.g., a tube) to extend through the greater palatine foramen 1302T and into the palatine canal 1302R. The delivery conduit 1397 can be relatively soft and flexible as described above. After extending the delivery conduit 1397 through the greater palatine foramen 1302T, the delivery device 1320 can deliver a therapeutic agent via a lumen 1340 in the delivery conduit 1397 into the palatine canal 1302R. In examples, the tissue seal created by the suction ports 1346 allows for the delivery device 1320 to collect and drain any of the therapeutic agent that leaks out of the greater palatine foramen 1302T after delivery (e.g., due to gravity). After delivering the therapeutic agent, the delivery conduit 1397 can be retracted and suction released (e.g., by eliminating a source of vacuum or negative pressure or by adjusting a valve to alter airflow through the delivery device 1320).

In examples described above, the therapeutic agent delivery member 234 can be implemented by a structure that is inserted into a natural opening or an opening formed by the boring element 236 (e.g., the delivery conduit 1297, 397 in FIGS. 12-13B). In some implementations, the structure of the therapeutic agent delivery member 234 can have a fixed size and/or shape. However, in other implementations, the therapeutic agent delivery member 234 can have a variable size and/or shape.

For example, the therapeutic agent delivery member 234 can have a relatively small diameter that can be inserted through a small opening and navigated into place with a lower level of required positional accuracy, reducing the time for placement and allowing lower skill-level operators to find routine success. However, the relatively small diameter of the therapeutic agent delivery member 234 may also limit a rate at which the therapeutic agent 238 can be delivered through the therapeutic agent delivery member and/or require a relatively high pressure to push the therapeutic agent 238 through the relatively small size of the therapeutic agent delivery member 234. In some instances, it may be advantageous for the therapeutic agent delivery member 234 to be inserted and removed from a region while having a relatively small diameter, and have a relatively larger diameter during a period of stable position when substances may be delivered through the therapeutic agent delivery member 234.

In some examples, the therapeutic agent delivery member 234 can include a tube (e.g., the delivery conduit 1297, 1397) that is constructed from a collapsible weave having a comparatively large diameter (e.g., approximately 1 mm) in a relaxed state. When a mechanical force is applied to the tube (e.g., a tensile force) the weave fibers may shift in orientation and collapse into a structure with a smaller diameter (e.g., approximately 0.5 mm). In examples, this process of using tension to collapse the weave fibers may also result in the tube having a slight increase in overall length.

In examples, the collapsible weave may be covered with an exterior tube to reduce (or minimize) leaks from the tube originating from gaps in the woven fibers. For instance, a flexible rubber or polymer tube may encase the woven components of the tube. In examples, an inner rubber tube along the interior surface of the woven fibers may accompany or replace the outer covering.

FIG. 14A shows a delivery device 1420 according to another example. As shown in FIG. 14A, the delivery device 1420 includes an elongated shaft 1422 and a grid of protrusions 1498 at a distal end 1454 of the elongated shaft 1422. The elongated shaft 1422 can include a lumen that is fluidly coupled to the protrusions 1498.

The protrusions 1498 can be made from a relatively soft and a relatively flexible material. For instance, the grid of protrusions 1498 can be manufactured from a soft material such as silicone that allows for each protrusion 1498 to collapse or invert completely in response to an application of a mechanical force or pressure (e.g., a pressure resulting from the protrusions 1498 being pressed against a tissue or bony structure). Each protrusion 1498 in the grid can be constructed to have a hollow fluid delivery lumen that is in fluid communication with the larger grid structure and the lumen in the elongated shaft 1422.

In some examples, the grid of the protrusions 1498 can be initially coated with a mild adhesive that allows for the protrusions 1498 to adhere to tissues, including moist soft tissues, for a relatively short period of time (e.g., less than approximately 30 minutes and/or less than approximately 15 minutes). Using endoscopic guidance, direct visualization, or another appropriate location method, the grid of protrusions 1498 can be placed in a general location of a natural orifice (e.g., the greater palatine foramen 102T or the sphenopalatine foramen 102G), and adhere to a tissue wall in this region. At least one of the protrusions 1498 can traverse the opening of the orifice and provide a conduit to deliver a therapeutic agent to a desirable tissue region (e.g., into the palatine canal 102R). The remainder of the protrusions 1498 that are not spatially-aligned with the opening will press against the tissue wall and collapse or become inverted, thereby closing their internal lumens in such a manner that prevents flow of a substance outward from these collapsed lumens. As an example, FIG. 14B shows the delivery device 1420 positioned against a tissue wall 1456 and two of the protrusions 1498 extending through an opening 1457 while a remainder of the protrusions 1498 are pressed against the tissue wall 1456 in a collapsed state.

While the delivery device 1420 is positioned against the tissue wall in this manner, a therapeutic agent source can provide the therapeutic agent (e.g., using an injection mechanism of a syringe) through the elongated shaft 1422 to the grid of the protrusions 1498 and out of the protrusion(s) 1498 that are spatially-aligned with the orifice and therefore not collapsed, resulting in transmission of the substance through the orifice and into a region of interest. One advantage of using a system such as the one described is that it reduces the required accuracy for placement of a delivery mechanism directly into a region such as the sphenopalatine foramen 102G or the greater palatine foramen 102T, which may allow for simpler delivery techniques.

In some of the examples described above, the therapeutic agent delivery member 234 can extend through a natural opening and/or an opening formed by the boring element 236 to deliver the therapeutic agent 238. However, as described above, the therapeutic agent delivery member 234 may not extend through the natural opening and/or the opening formed by the boring element 236 in other examples.

Figure 15:
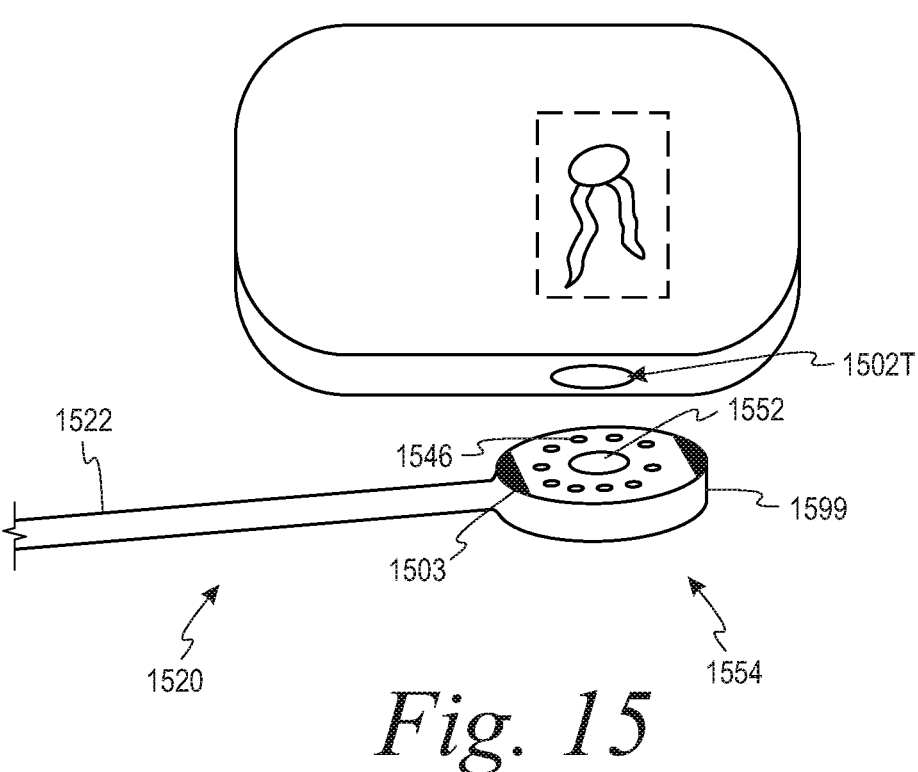
FIG. 15 shows a delivery device, according to another example.

For instance, FIG. 15 depicts a delivery device 1520 that can deliver a therapeutic agent without extending through a natural opening and/or an opening formed by the boring element 236. As shown in FIG. 15, the delivery device 1520 includes an elongated shaft 1522 comprised of a semi-rigid but malleable material (e.g., aluminum). The malleable material of the elongated shaft 1522 can be encapsulated by a layer of rubber or a polymer material to give the elongated shaft 1522 a soft feel that reduces the risk of noxious stimuli being produced via incidental contact of the body with soft or hard tissues.

As described above with respect to FIG. 2, the elongated shaft 1522 can include one or more lumens (e.g., the lumen(s) 240) that allow for a therapeutic agent to traverse the elongated shaft 1522 from a handpiece to a distal end 1554 of the delivery device 1520. The distal end 1554 of the delivery device 1520 can include a delivery pod 1599 which is configured to be positioned in a region of interest (e.g., at or nearby to a greater palatine foramen 1502T), and to eject the therapeutic agent through an output port 1552. Within examples, the output port 1552 can eject the therapeutic agent as a foam, mist, liquid, gas, high-pressure liquid stream, or in another form.

In some implementations, the delivery pod 1599 can optionally include other features intended to aid in delivering the therapeutic agent such as, for example, one or more suction ports 1546 and/or one or more image guidance sensors 1503. As examples, the image guidance sensors 1503 can be laser, infrared, ultrasound, or other optical or acoustic sensors. For instance, the image guidance sensors 1503 can be an ultrasound transducer operating in an A-mode configuration at a frequency between approximately 5 mega Hertz (MHz) and approximately 15 MHz. In this example, electronics to operate the image guidance sensors 1503 can be positioned in or proximate to the handpiece and the elongated shaft 1522 can include internal conduits (not shown) for wires connecting the image guidance sensors 1503 to the appropriate operational electronics. In some examples, the delivery pod 1599 can also be configured to assist the delivery of the therapeutic agent via electrophoresis or iontophoresis, and accordingly contain the electronics required to initiate these techniques.

In some examples, a delivery device can include a mouthpiece to facilitate access to the palatine canal 102R or other anatomical regions via the mouth. Given the proximity of the palatine foramen to the second and third molar as well as to the posterior ridge of the hard palate, examples that utilize teeth as anatomical landmarks may find usefulness in a number of subjects.

Figure 16:
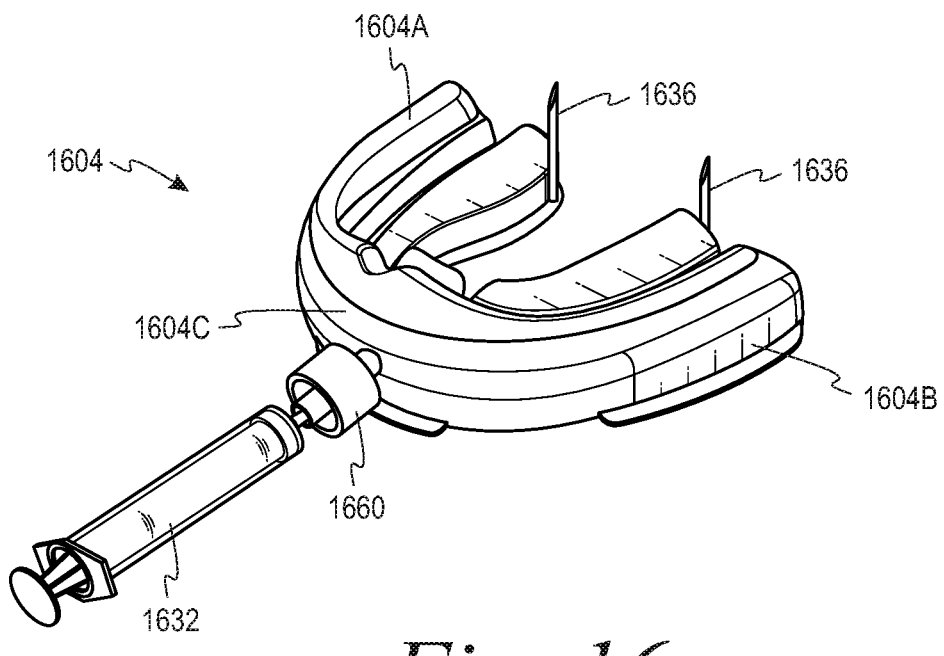
FIG. 16 shows a delivery device, according to another example.

FIG. 16 depicts a mouthpiece 1604 for delivering a therapeutic agent according to an example. As shown, the mouthpiece 1604 is configured to enter the mouth and interface with the molars bilaterally. The mouthpiece 1604 can have a U-shape with a first portion 1604A and a second portion 1604B extending from a center portion 1604C.

The mouthpiece 1604 can include a rigid penetration mechanism 1636 on the first portion 1604A and the second portion 1604B (i.e., on each side of the mouthpiece 1604). The rigid penetration mechanisms 1636 can be a needle that can pierce tissue (e.g., a hard plastic member machined into a point). The rigid penetration mechanisms 1636 can be positioned so that when the mouthpiece 1604 is placed in the mouth, the rigid penetration mechanisms 1636 lie posterior and slightly medial of the back molars. With the mouthpiece 1604 held in place by the teeth and/or a roof of the mouth, an operator can press the rigid penetration mechanisms 1636 (with or without the use of additional tooling) into the mucosa at or near the region of the greater palatine foramen 102T to form a passage directly into or adjacent to the palatine canal 102R.

In one example, after positioning the mouthpiece 1604 in the mouth, a subject can bite down on the mouthpiece 1604 such that the rigid penetration mechanisms 1636 penetrate into tissue at or near the location of the greater palatine foramen 102T. After the rigid penetration mechanisms 1636 form the passage into or nearby the palatine canal 102R, a therapeutic agent can be delivered into the palatine canal 102R through respective lumens in the rigid penetration mechanisms 1636.

As shown in FIG. 16, the mouthpiece 1604 can include a substance input port 1660 (e.g., a luer fitting) that can couple to a therapeutic agent source 1632 (e.g., a syringe). In this example, depressing a plunger on therapeutic agent source 1632 injects the therapeutic agent into the mouthpiece 1604. The therapeutic agent then flows through the mouthpiece 1604 via one or more internal lumens and exits the rigid penetration mechanisms 1636 into the palatine canal 102R.

In one implementation, the substance input port 1660 can receive the therapeutic agent in a liquid form. In another implementation, the substance input port 1660 can receive the therapeutic agent in a gas form (e.g., via a connection to a pressurized source of a gas or mist).

Referring to FIG. 17, a method 1700 for using the mouthpiece 1604 to deliver the therapeutic agent is shown. As shown in FIG. 17, the method 1700 can include the following steps: (1) applying a topical or needle injectable anesthetic, for example a lidocaine gel or injection, to the tissues along the gum line and/or in the region of the mouth proximate to the greater palatine foramen at block 1702; (2)

inserting the mouthpiece 1604 into the subject's mouth at block 1704; (3) performing an action that results in the rigid penetration mechanisms 1636 of the mouthpiece 1604 traversing the greater palatine foramen 102T or otherwise penetrating tissue to access the palatine canal 102R or a tissue region proximate to the palatine canal 102R at block 1706; and (4) delivering a therapeutic agent via the rigid penetration mechanisms 1636 of the mouthpiece 1604 to the nerves in the palatine canal 102R at block 1708. In an example, step (2) may also include a step of placing an anesthetic substance such as a gel or foam onto the mouthpiece 1604 prior to inserting it into the subject's mouth.

FIGS. 18A-18D depict a delivery device in the form of a mouthpiece 1804 according to another example. The mouthpiece 1804 can facilitate access to the palatine canal 102R, pterygopalatine fossa, and/or other anatomical regions via the mouth. Given the proximity of the palatine foramen 102T to the second and third molar as well as the posterior ridge of the hard palate, examples that utilize teeth as anatomical landmarks may find usefulness in a number of subjects.

As shown in FIGS. 18A-18D, the mouthpiece 1804 can include an access port 1860, a topical anesthetic well 1806, a bilateral working lumen 1808, a molar housing 1810, a front teeth housing 1812, a translatable introducer port 1814, and needle introducers 1816. The mouthpiece 1804 can enter a mouth and interface with the molars bilaterally and the front teeth. The topical anesthetic well 1806 is configured to hold a topical anesthetic gel or one or more soaked pledgets against the roof of the mouth while inhibiting (or preventing) the anesthetic from migrating posteriorly to the throat.

On each side of the mouthpiece 1804, the molar housing 1810 can have a size that is adjustable to facilitate fitting the mouthpiece 1804 securely around the molars. Within examples, the molar housings 1810 can be adjusted in an anterior-posterior manner to accommodate anatomical differences and to ensure an exit port of the bilateral working lumen 1808 is aligned with the palatine foreman on both sides.

Figures 18A, 18B:
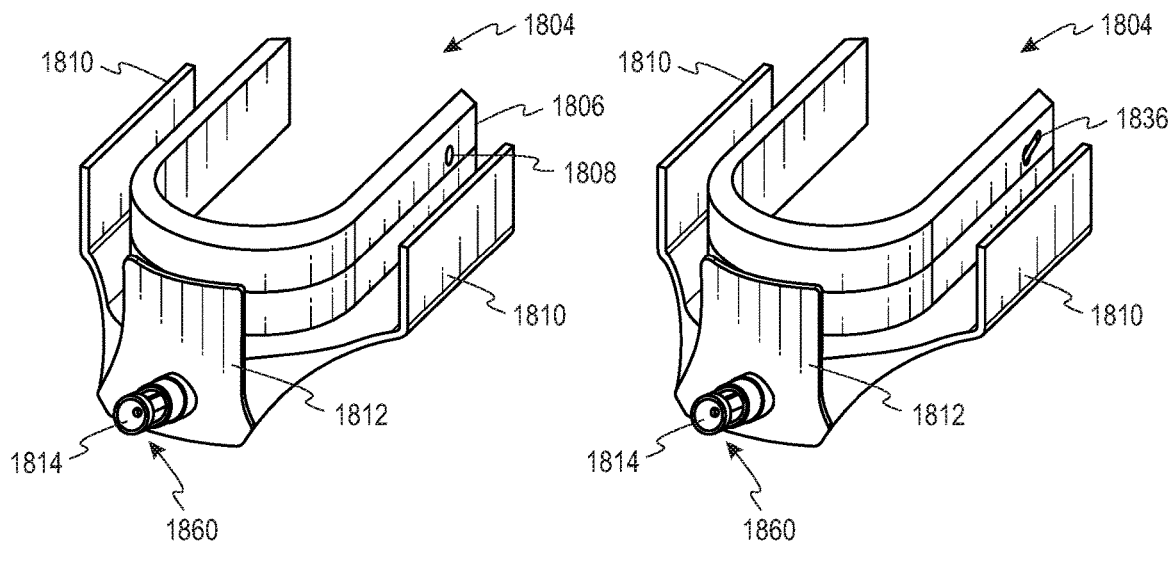
FIG. 18A shows a delivery device in a first state, according to an example.
FIG. 18B shows the delivery device of FIG. 18A in a second state, according to an example.
Figures 18C, 18D:
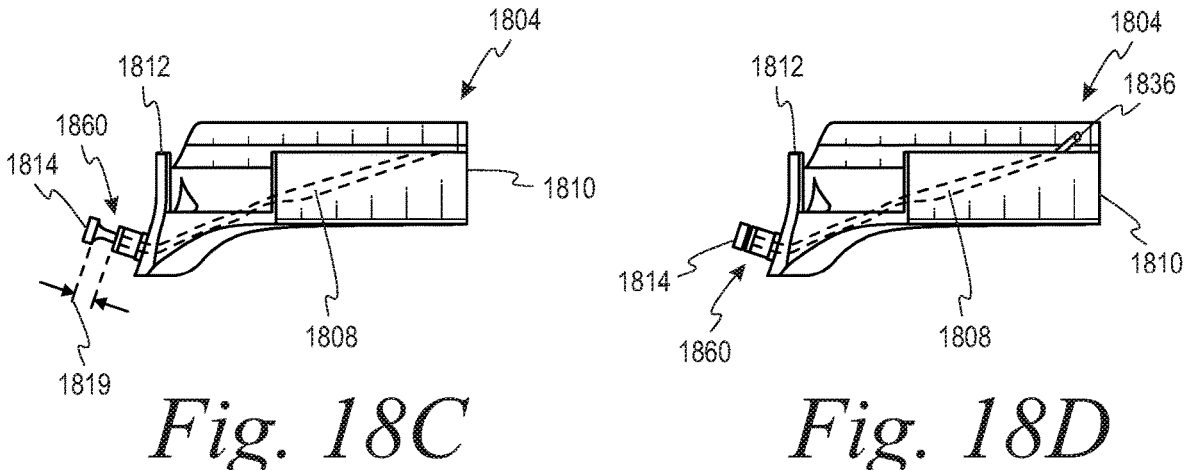
FIG. 18C shows a side view of the delivery device shown in FIG. 18A, according to an example.
FIG. 18D shows a side view of the delivery device shown in FIG. 18B, according to an example.
Figure 19:
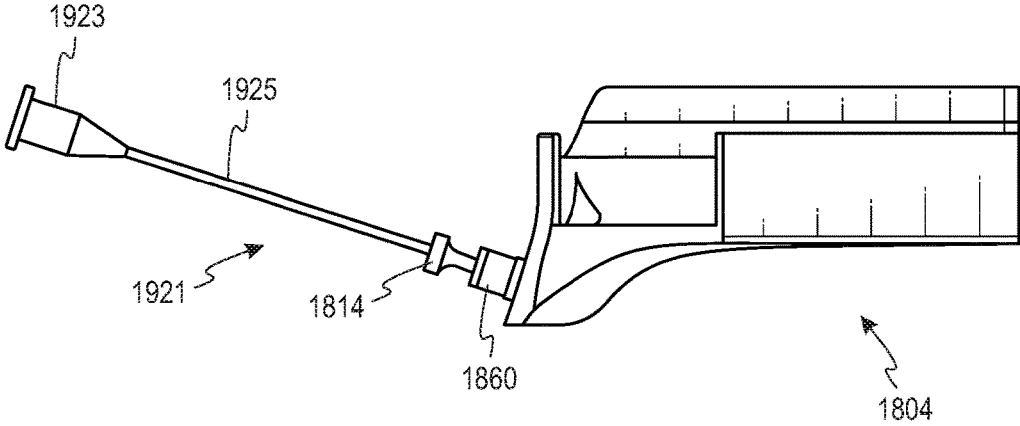
FIG. 19 show a delivery device in a first state, according to another example.
Figure 20:
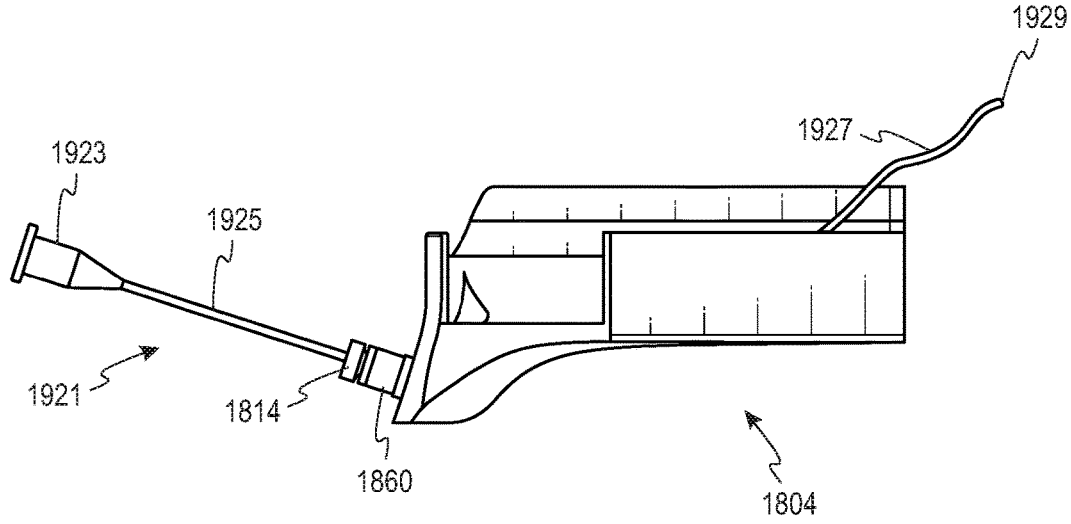
FIG. 20 shows the delivery device of FIG. 19 in a second state, according to an example.
Figures 21, 22:
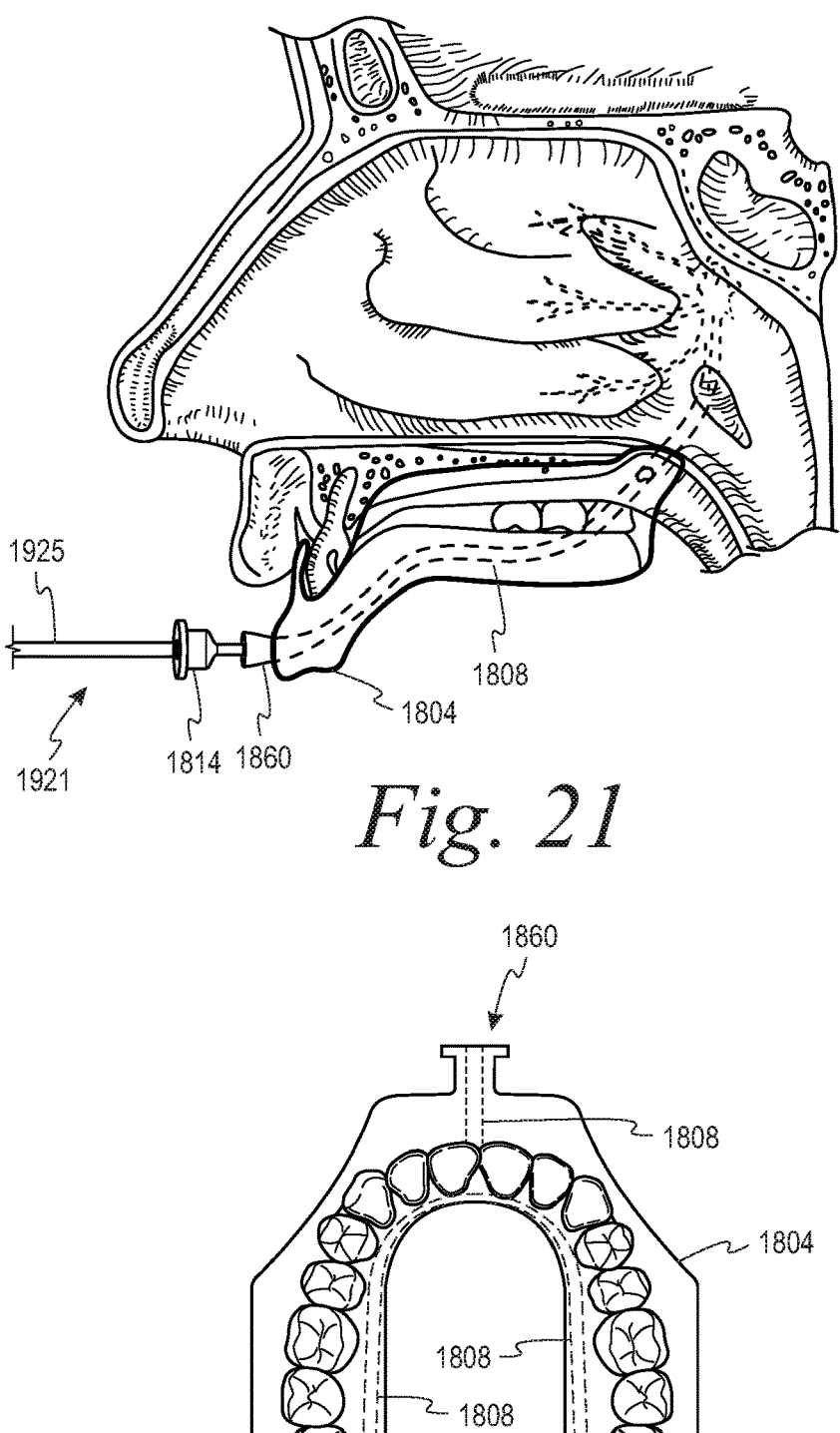
FIG. 21 shows the delivery device of FIG. 18A in a mouth, according to an example.
FIG. 22 shows a bottom view of the delivery device of FIG. 18A placed in a subject's mouth, according to an example.

As shown in FIGS. 18C-18D, the bilateral working lumen 1808 can run internally through each side of the mouthpiece 1804 and terminate at the access port 1860 at an anterior side of the mouthpiece 1804. The access port 1860 can be positioned below the front teeth and extend just beyond the teeth to give unobstructed access to the bilateral working lumen 1808.

In some examples, the access port 1860 can rotate 180 degrees relative to the mouthpiece 1804. Rotating the access port 1860 can modify an access to the bilateral working lumen 1808 (e.g., by actuating a valve in the access port 1860). In one example, the access port 1860 can have three states: (i) a first state in which the access port 1860 is coupled to the bilateral working lumen 1808 on a first side of the mouthpiece 1804, (ii) a second state in which the access port 1860 is coupled to the bilateral working lumen 1808 on a second side of the mouthpiece 1804, and (iii) a third state in which the access port 1860 is coupled to the bilateral working lumen 1808 on the first side of the mouthpiece 1804 and the second side of the mouthpiece 1804. This can facilitate selectively delivering a therapeutic agent to tissues and/or nerves on a single side or both sides of the mouthpiece 1804.

The mouthpiece 1804 can also include an introducer needle 1836 in the bilateral working lumen 1808 on each side of the mouthpiece 1804. In FIGS. 18A and 18C, the introducer needles 1836 are retracted in the bilateral working lumens 1808 on each side of the mouthpiece 1804. In FIGS. 18B and 18D, the introducer needles 1836 extend outwardly from the bilateral working lumens 1808 on each side of the mouthpiece 1804 (e.g., extending by approximately 10 mm from the bilateral working lumens 1808).

In an example, the introducer needles 1836 can be actuated between a retracted position shown in FIGS. 18A, 18C and an extend position shown in FIGS. 18B, 18D by translating the translatable introducer port 1814 in an axial direction. In one implementation, the translatable introducer port 1814 is configured to translate a distance 1819 of approximately 1 mm to approximately 20 mm (or, in another implementation, approximately 5 mm to approximately 10 mm) in the axial direction.

Within examples, the introducer needles 1836 can be made of a hard plastic or a metal similar to that used to construct a hypodermic needle. The gauge of the introducer needles 1836 can range from 16 gauge to 31 gauge. A size of the introducer needles 1836 can be based on a type of the therapeutic agent to be delivered. For instance, in an implementation in which the therapeutic agent is a fluid, the introducer needles 1836 can have a size between 25 gauge and 31 gauge. In another implementation in which the therapeutic agent is not a fluid (e.g., a gas), the introducer needles 1836 can have a size between 16 gauge and 22 gauge.

In operation, a procedure can be performed using the mouthpiece 1804 by: (1) applying a topical anesthetic into the anesthetic well 1806 (e.g., a lidocaine or tetracaine gel or solution); (2) inserting the mouthpiece 1804 into the subject's mouth ensuring that the molar housings 1810 are aligned properly and that the front teeth housing 1812 is affixed to the front teeth; (3) waiting for a period of time (e.g., approximately 5-15 minutes) for the topical anesthetic to numb the roof of the mouth; (4) rotating the access port 1860 to a state selected from among the first state, the second state, and the third state; (5) preparing a syringe of 1-5 cc of an anesthetic agent with or without a decongesting agent; (6) attaching the syringe to the translatable introducer port 1814 and deploying introducer needles 1836 into the roof of the mouth by translating the translatable introducer port 1814 by the distance 1819 (e.g., until the translatable introducer port 1814 contacts the access port 1860); (7) aspirating the syringe and once confirming clear to inject; (8) injecting the therapeutic agent through the introducer needles 1836 into the rough of the mouth and into a palatine foramen 102T.

The method described above can achieve anesthetizing a substantial portion of the posterior region of the nasal cavities as well as the roof of mouth by anesthetizing a relatively large percentage of the nasal and oral branches of the maxillary nerve. This method can also be used to help control the bleeding in the nasal cavity during nasal surgical procedures as a main blood supply to the nose passes through this canal and fossa. The article written by Peter-John Wormald, M.D, "An Evaluation of Effect of Pterygopalatine fossa Injection with Local Anesthetic and Adrenalin in the Control of Nasal Bleeding during Endoscopic sinus surgery" is incorporated by reference.

In some implementations, it may be desirable to reach the pterygopalatine fossa to deliver a more controlled amount of the therapeutic agent and to ensure the therapeutic agent gets to the target site in the fossa (e.g. a Sphenopalatine Ganglion). Accessing the fossa via the palatine foramen 102T may lead to trauma to artery, nerves, and tissue that course through the canal. In the examples described below, a risk of such trauma is reduced (or minimized) and provides a more reliable and more safe way of cannulating the fossa and delivering the therapeutic agent.

FIGS. 19-22 show the mouthpiece 1804 of FIG. 18 and a guidewire needle 1921 for cannulating the pterygopalatine fossa according to an example. The guidewire needle 1921 can include a guidewire entry port 1923, a proximal section 1925, a distal section 1927, a distal tip 1929 having a delivery exit port, and a central lumen that can extend from the guidewire entry port 1923 to the delivery exit port at the distal tip 1929. The proximal section 1925 can be made from a semi-rigid material, and the distal section 1927 can be made from a flexible material.

The distal tip 1929 of the guidewire needle 1921 can be inserted into the access port 1860 of the mouthpiece 1804. The guidewire needle 1921 and the access port 1860 can have respective sizes and/or shapes that are suitable to allow the guidewire needle 1921 to translate through the access port 1860 with relative ease and adequate pushability.

The guidewire entry port 1923 can be configured to couple with a syringe. In an example, the guidewire entry port 1923 can be made from stainless steel and/or a hard to semi-hard plastic (e.g. Polycarbonate). As described above, the guidewire needle 1921 can include the proximal section 1925 and the distal section 1927. The proximal section 1925 can be sufficiently rigid to withstand and transfer torque and translating forces from the user to the distal end with minimal loss. As one example, the proximal section 1925 can include a stainless steel hypotube.

The distal section 1927 can be flexible while still being translatable via a proximally-applied force and rotatable. In one example, the distal section 1927 can include a round or flat wire that is closed wound clockwise and/or counter-clockwise (i.e., wires can be touching and the central lumen can be closed off). The distal section 1927 of the guidewire needle 1921 can terminate at the distal tip 1929. The distal tip 1929 can have a size and/or a shape that is atraumatic to help mitigate (or prevent) the risk of a guidewire needle 1921 puncturing an artery wall or tearing through tissue.

In some implementations, the distal tip 1929 can include a radiopaque marker and/or an illumination element that can emit light. The radiopaque marker and/or the illumination element of the distal tip 1929 can help the user to track a location of the distal tip 1929 of the guidewire needle 1921 as it passes through tissue and/or a bony structure. In some implementations, when the distal tip 1929 includes the illumination element, the translation of the guidewire needle 1921 can be observed in a nasal passage or potentially through the side of the face.

As described above, the guidewire needle 1921 can include a central lumen. The central lumen can allow the therapeutic agent to pass from one end of the other without leaking. At a distal end of the central lumen is the delivery exit port at which the therapeutic agent exits the central lumen. In one example, the distal tip 1929 of the guidewire needle 1921 can extend to a range of approximately 25 mm to approximately 50 mm from the bilateral working lumen 1808 (shown in FIG. 22 extending in in the molar housing 1810).

A method for using the mouthpiece 1804 and the guidewire needle 1921 can include the following steps: (1) applying a topical anesthetic into the anesthetic well 1806 (e.g., a lidocaine or tetracaine gel or solution); (2) inserting the mouthpiece 1804 into the subject's mouth ensuring that the molar housings 1810 are aligned properly and that the front teeth housing 1812 is affixed to the front teeth; (3) waiting for a period of time (e.g., approximately 5-15 minutes) for the topical anesthetic to numb the roof of the mouth; (4) rotating the access port 1860 to a state selected from among the first state, the second state, and the third state; (5) preparing a syringe of 1-5 cc of an anesthetic agent with or without a decongesting agent; (6) deploying introducer needles 1836 into the roof of the mouth by translating the translatable introducer port 1814 by the distance 1819 (e.g., until the translatable introducer port 1814 contacts the access port 1860); (7) attaching the syringe to the guidewire needle 1921; (8) feeding the guidewire needle 1921 through the introducer needles 1836 into the palatine canal and advancing the guidewire needle 1921 until the distal tip 1929 of the guidewire needle 1921 reaches the fossa; (9) aspirating the syringe and once confirming clear to inject; (8) inject the therapeutic agent through the guidewire needle 1921 into the fossa.

Within examples, the mouthpiece 1804 can be configured to surround one or more teeth to assist with positioning and stability. In some examples, the mouthpiece 1804 can interface primarily with the hard or soft palate and interface only with the medial edges of one or more of the teeth or not interface with the teeth at all.

In some implementations, the mouthpiece 1804 can be manufactured in one or more pre-configured sizes and is not customized for a particular patient. In other implementations, the mouthpiece 1804 can be customized to fit a specific patient, for example, based on a mold taken from the patient's mouth, or based on a CT/MR or other scan of the relevant patient anatomy. The mouthpiece 1804 can be constructed of a soft material such as a silicone or can be constructed of multiple materials, for example a plastic overmold with an internal stainless steel backbone to provide increased mechanical stability.

In some examples, the mouthpiece 1804 can include one or more sensors that assist in locating the foramen, for example the greater palatine foramen 102T, to guide access of a substance or a substance delivery mechanism into the palatine canal 102R. In one implementation, the sensor(s) can guide the gross placement of the mouthpiece 1804 itself. In some implementations, the sensor(s) can allow for fine-tuning of the position of the mouthpiece 1804 or portions of the mouthpiece 1804 to more closely align with the foramen 102T.

In some examples, the sensor(s) can involve imaging modalities that allow a user to directly visualize the foramen 102T (e.g., the sensor(s) can record video or photographs of nearby structures during placement that are transmitted with or without the use of video cables to a monitor where it is viewed by an operator).

In some examples, the mouthpiece 1804 can include a lumen (e.g., the bilateral working lumens 1808) adapted to interface with a syringe or a similar substance-introduction mechanism at the proximal end which terminates with a delivery tube at the distal end. This delivery tube at the distal end of the lumen can be configured to enter the foramen when positioned properly via camera guidance. Proximate to the delivery tube is one or more cameras adapted to visualize structures in a manner so as to guide positioning. In examples, a light source may also be proximate to the delivery tube in order to illuminate structures in the field suitably for visualization. In examples, the delivery tube, camera(s), and light source(s) can be present exclusively on one side (left or right) of the mouthpiece 1804. In alternate examples, these components are positioned bilaterally.

In examples, the delivery tube, camera(s), and light source(s) are mounted on an appendage of the mouthpiece 1804 that is capable of moving independently from a main body of the mouthpiece 1804. For example, a small appendage may attach to the main body of the mouthpiece 1804 near its posterior end(s) via a ball joint or another mechanism that allows for the appendage to move independently of the main body of the mouthpiece 1804. In an example method of use, the mouthpiece is placed by the operator in the mouth of the patient and secured in position by fitting it snugly around the upper teeth. The camera and/or light source may be activated and the relative position of the appendage(s) containing the delivery tube(s) using video or photographic feedback displayed on a screen located external to the patient's mouth may be adjusted. This adjustment may be performed until the delivery tube enters or otherwise is positioned in a desired location with the foramen. Once placed, the delivery of a therapeutic agent may be initiated, for example by depressing the plunger on a syringe interfacing with the mouthpiece or by adjusting a valve on the mouthpiece 1804 to enable flow of a substance through the lumen and into the palatine canal via the delivery tube.

Examples can alternatively or additionally utilize non-photographic sensors. For instance, examples can employ visualization techniques involving medical imaging technologies, such as ultrasound, optical coherence tomography, or laser. In examples, an ultrasound transducer or laser emitter is mounted near the posterior portion of a mouthpiece to guide the insertion or placement of one or more delivery tubes. In examples, an ultrasound transducer is adapted to operate in A-mode and detect when an echo signal is reduced in amplitude or delayed in time (or both), indicating that the transducer is transmitting into the open foramen and not emitting signals that are reflected strongly at the interface of the hard or soft palate. In examples, coupling balloons containing gels or fluids are utilized to ensure proper acoustic coupling of emitted ultrasound signals from the transducer into tissues inside the mouth. In variation examples, a transducer array is configured to be utilized in B-mode and a live ultrasound image is displayed on a video screen, allowing the user to adapt the position of delivery tubes in real-time. In variation examples, optical-based techniques similarly may be used to map the surface of the roof of the mouth, using signal irregularities originating from the presence of the open foramen as a means to identify the entry point into the palatine canal.

Within examples, the devices, systems, and methods described herein can be additionally or alternatively configured to deliver an object into or proximate to a region of interest. For instance, in some examples, the devices, systems and methods can be configured to deliver the therapeutic agent 238 (e.g., a drug/pharmaceutical agent or anesthetic agent) in a solid form, which can provide for a prolonged release over time. In one implementation, the therapeutic agent 238 can be mixed into a solid comprised of an absorbable sugar that dissolves over time when exposed to moisture in the environment of mucosal tissues. In another implementation, a drug may be manufactured into a thin film or gelatinous substrate that similarly dissolves after exposure to tissues in the region of interest. In some implementations, a mechanism for substrate degradation can be triggered by body heat and/or moisture. Within examples, the degradation of the solid or substrate triggers the release of the therapeutic agent 238, with the release being gradual and in proportion to the timescale of the degradation. As described above, the delivery device 220, 320, 420, 520, 620, 720, 820, 920, 1020, 1120, 1220, 1320, 1420, 1520, 1620, 1804 can deliver the solid therapeutic agent to a natural orifice and/or a passage formed using the boring element 236 to deliver the solid therapeutic agent to regions of interest.

Within examples, the delivery devices and methods described above can include one or more components for performing a cryotherapy procedure (e.g., such as a cryo-ablation procedure). For instance, the delivery devices 220, 320, 420, 520, 620, 720, 820, 920, 1020, 1120, 1220, 1320, 1420, 1520, 1620, 1804 can include a cryogen source for storing a cryogen (e.g., nitrous oxide, liquid carbon dioxide, and/or liquid chlorofluorocarbon) at a proximal portion, an applicator having a cryotherapy delivery feature that can use the cryogen to apply thermal energy to a target tissue, and a lumen that couples the cryogen source to the cryogen delivery feature.

In some examples, the cryotherapy components can be integrated with the features of the delivery device described above. This can beneficially allow for the delivery device to deliver the therapeutic agent, warm the protrusions and/or needles, and/or form a passage before, during, or after applying cryotherapy to a target tissue. Additional details regarding devices that combine cryotherapy components with features for delivering a therapeutic agent (e.g., an anesthetic agent) are described in U.S. Provisional Application No. 62/861,591, filed Jun. 14, 2019, the contents of which is hereby incorporated by reference in its entirety. In other examples, the cryotherapy components can be implemented in a second device that is separate from the components for forming the passage, delivering the therapeutic agent, and/or generating heat described above.

Referring now to FIG. 23, a flowchart for a method 2300 for delivery of a therapeutic agent to at least one of a palatine canal or a pterygopalatine fossa of a patient is shown according to an example. At block 2310, the method 2300 includes inserting a delivery device into a nasal cavity of a patient. The delivery device includes an elongated shaft with a proximal end and a distal end, a handpiece coupled to the proximal end of the elongated shaft, and a boring element disposed on the distal end of the elongated shaft. At block 2312, the method 2300 includes advancing the distal end of the elongated shaft to a position proximate to a palatine bone within the nasal cavity. At block 2314, the method 2300 includes actuating the boring element to form a passage in the palatine bone between the nasal cavity and a palatine canal of the patient. At block 2316, the method 2300 includes delivering a therapeutic agent into the palatine canal.

FIGS. 24-34 depict additional aspects of the method 2300 according to further examples. As shown in FIG. 24, actuating the boring element at block 2314 can include ejecting a boring fluid in a fluid stream from the elongated shaft to the palatine to bore the passage through the palatine bone at block 2318.

As shown in FIG. 25, delivering the therapeutic agent at block 2316 can include ejecting the fluid stream of the therapeutic agent from the elongated shaft through the passage in the palatine bone and into the palatine canal at block 2320.

In an example, the delivery device can include a therapeutic agent delivery member at distal portion of the elongated shaft. As shown in FIG. 26, delivering the therapeutic agent at block 2316 can include ejecting a fluid stream of the therapeutic agent from the therapeutic agent delivery member of the elongated shaft through the passage in the palatine bone and into the palatine canal at block 2322.

In an example, the boring element can include a needle. As shown in FIG. 27, actuating the boring element at block 2314 can include projecting the needle laterally away from a distal portion of the elongated shaft and through the palatine bone at block 2324.

As shown in FIG. 28, projecting the needle laterally away from a distal portion of the elongated shaft and through the palatine bone at block 2324 can include inflating an expandable member coupled to the needle at block 2326.

As shown in FIG. 29, projecting the needle laterally away from a distal portion of the elongated shaft and through the palatine bone at block 2324 can include releasing a compressed spring coupled to the needle at block 2328.

As shown in FIG. 30, the method 2300 can include, prior to actuating the boring element at block 2314, positioning the distal end of the elongated shaft such that the boring element is adjacent to the palatine bone by inflating an expandable member coupled to the distal end of the elongated shaft so as to stabilize the needle while the needle penetrates through the palatine bone at block 2330.

Figure 31:
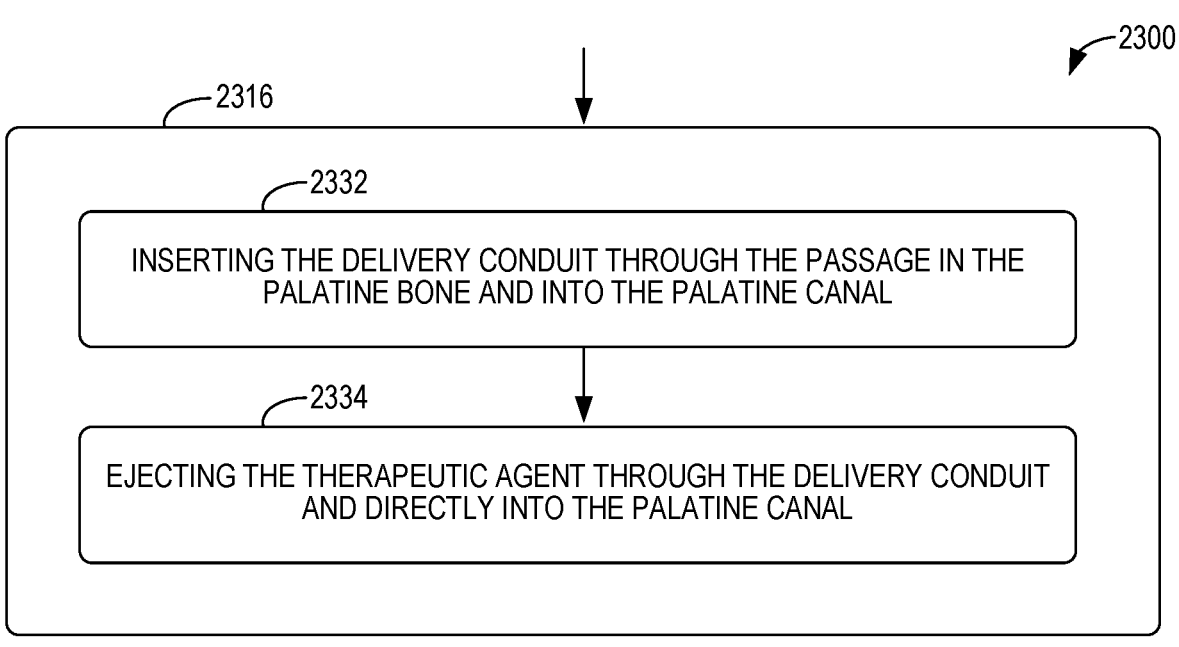
FIG. 31 shows a method for delivery of a therapeutic agent to at least one of a palatine canal or a pterygopalatine fossa of a patient that can be used with the method of FIG. 23, according to an example.

In an example, the delivery device can further include a therapeutic agent delivery member disposed on a distal portion of the elongated shaft and having a delivery conduit. As shown in FIG. 31, delivering the therapeutic agent into the palatine canal at block 2316 can include (i) inserting the delivery conduit through the passage in the palatine bone and into the palatine canal at block 2332, and (ii) ejecting the therapeutic agent through the delivery conduit and directly into the palatine canal at block 2334.

Figure 32:
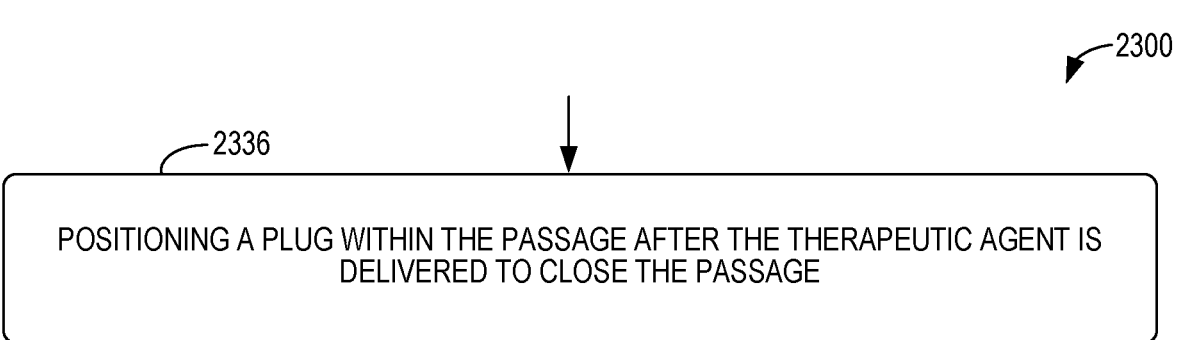
FIG. 32 shows a method for delivery of a therapeutic agent to at least one of a palatine canal or a pterygopalatine fossa of a patient that can be used with the method of FIG. 23, according to an example.

As shown in FIG. 32, the method 2300 can also include positioning a plug within the passage after the therapeutic agent is delivered to close the passage at block 2336.

In an example, the delivery device further can include a cryotherapy delivery feature. As shown in FIG. 33, the method 2300 can further include positioning the cryotherapy delivery feature at a position proximate to a target nerve in the nasal cavity at block 2338, and cryo-ablating, using the cryotherapy delivery feature, the target nerve to reduce a symptom of rhinitis after delivery of the therapeutic agent into the palatine canal at block 2340.

As shown in FIG. 34, the method 2300 can further include inserting a second device into the nasal cavity of the patient at block 2342. The second device can include a second shaft with a second proximal end and a second distal end, a second handpiece coupled to the second proximal end, and a therapeutic agent delivery member disposed on the second distal end. The method 2300 can also include advancing the second distal end of the second shaft through the passage and into the palatine canal at block 2344, and delivering a therapeutic agent into the palatine canal with the therapeutic agent delivery member at block 2346.

Figure 35:
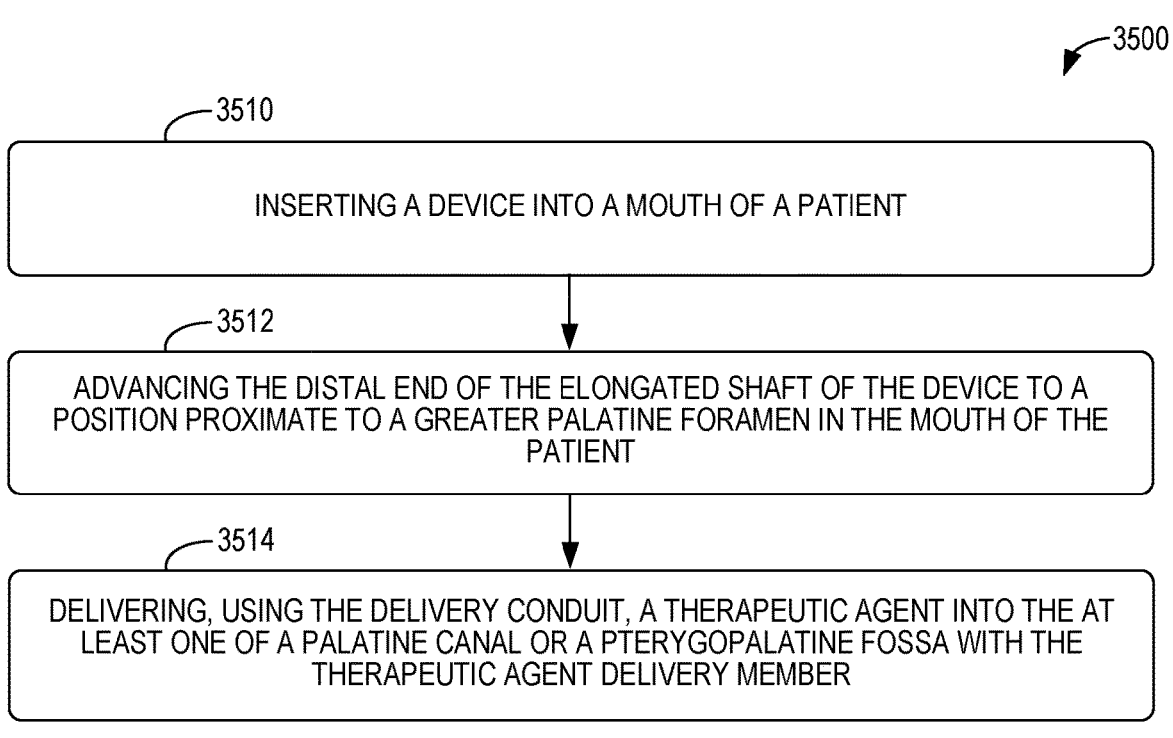
FIG. 35 shows a method for delivery of a therapeutic agent to at least one of a palatine canal or a pterygopalatine fossa of a patient according to another example.

Referring now to FIG. 35, a flowchart for a method 3500 for delivering a therapeutic agent to at least one of a palatine canal or a pterygopalatine fossa of a patient is shown according to another example. At block 3510, the method 3500 includes inserting a device into a mouth of a patient. The device includes an elongated shaft with a proximal end and a distal end, an access port coupled to the proximal end of the elongated shaft, and a therapeutic agent delivery member disposed at a distal portion of the elongated shaft. The therapeutic agent delivery member includes a delivery conduit. At block 3512, the method 3500 includes advancing the distal end of the elongated shaft of the device to a position proximate to a greater palatine foramen in the mouth of the patient. At block 3514, the method 3500 includes delivering, using the delivery conduit, a therapeutic agent into the at least one of a palatine canal or a pterygopalatine fossa with the therapeutic agent delivery member.

Figure 36:
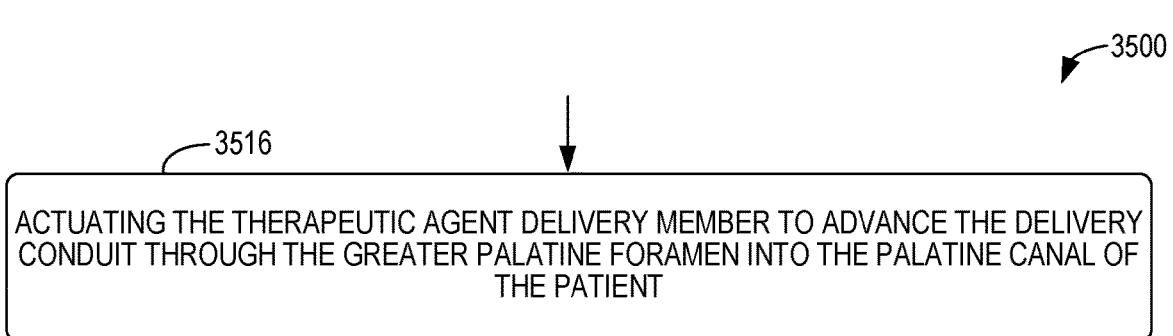
FIG. 36 shows a method for delivery of a therapeutic agent to at least one of a palatine canal or a pterygopalatine fossa of a patient that can be used with the method of FIG. 35, according to an example.
Figure 37:
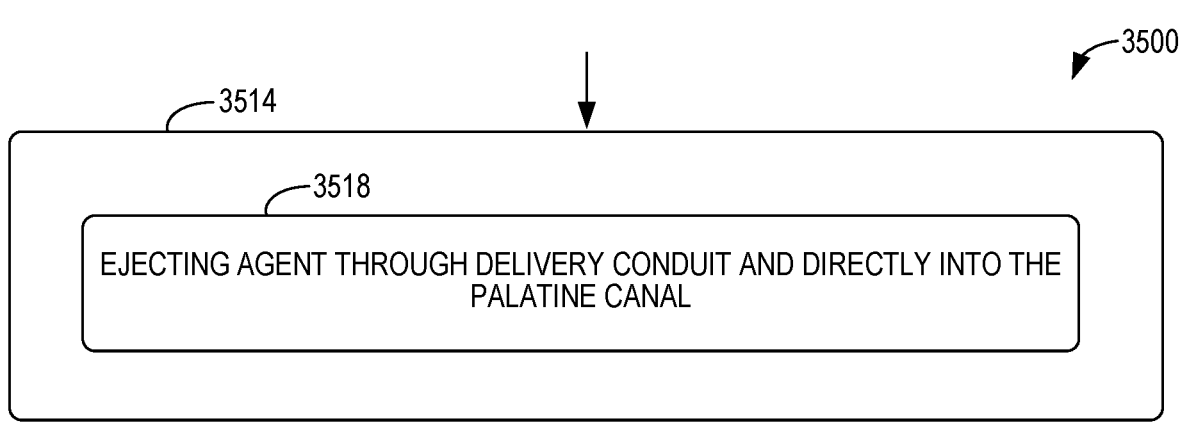
FIG. 37 shows a method for delivery of a therapeutic agent to at least one of a palatine canal or a pterygopalatine fossa of a patient that can be used with the method of FIG. 36, according to an example.

FIGS. 36-39 depict additional aspects of the method 3500 according to further examples. As shown in FIG. 36, the method 3500 can also include actuating the therapeutic agent delivery member to advance the delivery conduit through the greater palatine foramen into the palatine canal of the patient at block 3516. As shown in FIG. 37, delivering the therapeutic agent at block 3514 can include ejecting agent through delivery conduit and directly into the palatine canal at block 3518.

Figure 38:
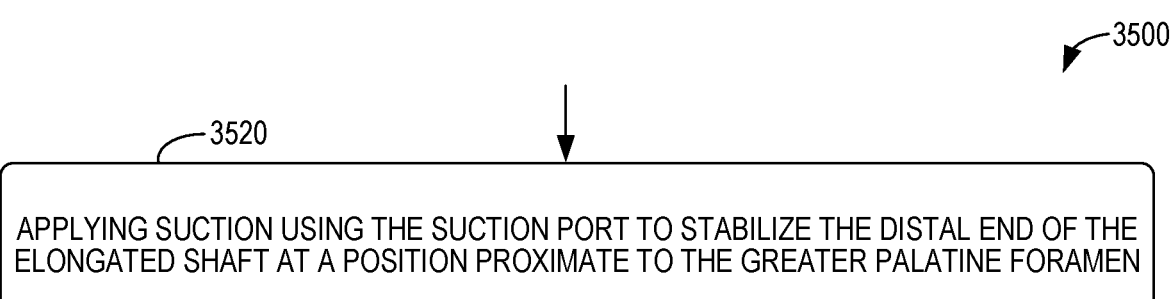
FIG. 38 shows a method for delivery of a therapeutic agent to at least one of a palatine canal or a pterygopalatine fossa of a patient that can be used with the method of FIG. 35, according to an example.
Figure 39:
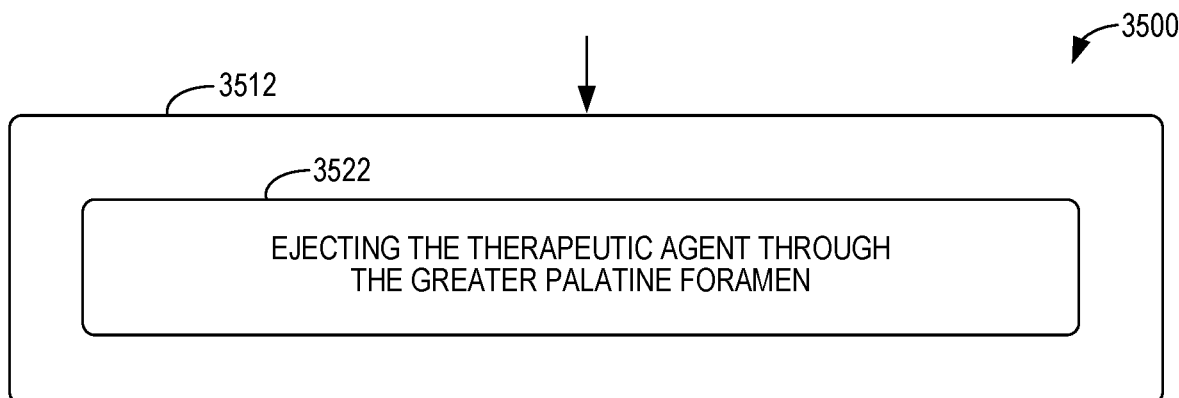
FIG. 39 shows a method for delivery of a therapeutic agent to at least one of a palatine canal or a pterygopalatine fossa of a patient that can be used with the method of FIG. 35, according to an example.

In an example, the delivery device can also include a suction port disposed on the distal end of the elongated shaft. As shown in FIG. 38, the method 3500 can include applying suction using the suction port to stabilize the distal end of the elongated shaft at a position proximate to the greater palatine foramen at block 3520. As shown in FIG. 39, delivering the therapeutic agent at block 3514 can include ejecting the therapeutic agent through the greater palatine foramen at block 3522.

Referring now to FIG. 40, a flowchart for a method 4000 for delivering a therapeutic agent to at least one of a palatine canal or a pterygopalatine fossa of a patient is shown according to another example. At block 4010, the method 4000 includes inserting a mouthpiece into a mouth of a patient. The mouthpiece is u-shaped. The mouthpiece includes a well configured to receive teeth of the patient. The mouthpiece includes an introducer needle. At block 4012, the method 4000 includes positioning the mouthpiece so that the teeth are received in the well and the introducer needle is inserted in a greater palatine foramen of the patient. At block 4014, the method 4000 includes delivering a pharmaceutical agent through the introducer needle and into the greater palatine foramen into a palatine canal of the patient.

Referring now to FIG. 41, a flowchart for a method 4100 for delivery of a therapeutic agent to a canal in a skull of a patient containing a nerve is shown according to an example. At block 4110, the method 4100 includes inserting a device into a nasal cavity of a patient. The device includes a shaft with a proximal end and a distal end, a handpiece coupled to the proximal end of the shaft, and a boring element disposed on the distal end of the shaft. At block 4112, the method 4100 includes advancing the distal end of the shaft to a position proximate to a bone within the nasal cavity at least partially defining a canal in the skull of the patient containing a nerve. At block 4114, the method 4100 includes actuating the boring element to create a passage in the bone between the nasal cavity and the canal. At block 4116, the method 4100 includes delivering a therapeutic agent into the canal. In one example, the bone is a sphenoid bone and the canal is a vidian canal.

By the term "approximately" or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to explain the principles of the examples, the practical application, and to enable others of ordinary skill in the art to understand the disclosure for various examples with various modifications as are suited to the particular use contemplated.

What is claimed is:

1. A delivery device for delivering a therapeutic agent to at least one of a palatine canal or a pterygopalatine fossa of a patient, the delivery device comprising:

an elongated shaft with a proximal end and a distal end, wherein the elongated shaft comprises at least one lumen that extends through the elongated shaft to an output port at a distal portion of the elongated shaft, wherein the output port is proximal of the distal end of the elongated shaft;

a handpiece coupled to the proximal end of the elongated shaft; and a boring element at the distal portion of the elongated shaft and configured to form a passage in a palatine bone;

a therapeutic agent delivery member configured to deliver a therapeutic agent via the output port of the elongated shaft to the passage formed by the boring element; and one or more user control devices on the handpiece, wherein the one or more user control devices are operable to cause the boring element to form the passage in the palatine bone, wherein the boring element comprises: a needle that is configured to move through the output port and away from the elongated shaft to form the passage in the palatine bone responsive to an operation of the one or more user control devices, and a needle actuator that is configured to apply a force to the needle to cause the needle to (i) move through the output port and (ii) penetrate through the palatine bone responsive to operation of the one or more user control devices.

2. The delivery device of claim 1, wherein the needle actuator comprises an expandable member coupled to the needle, wherein the expandable member is configured to be inflated to project the needle from the distal portion of the elongated shaft and through the palatine bone.

3. The delivery device of claim 1, wherein the needle actuator comprises a compressed spring coupled to the needle, wherein the compressed spring is configured to be released to project the needle from the distal portion of the elongated shaft and through the palatine bone.

needle, wherein the compressed spring is configured to be released to project the needle from the distal portion of the elongated shaft and through the palatine bone.

4. The delivery device of claim 1, further comprising one or more stabilizer features configured to retain the delivery device at a relatively fixed position while the boring element forms the passage in the palatine bone and/or while the therapeutic agent delivery member delivers the therapeutic agent.

5. The delivery device of claim 4, wherein the one or more stabilizer features include an expandable member coupled to the distal end of the elongated shaft.

6. The delivery device of claim 4, wherein the one or more stabilizer features include one or more suction ports.

7. The delivery device of claim 1, further comprising one or more sensors configured to indicate whether the distal end of the elongated shaft is proximate to a tissue surface.

8. The delivery device of claim 7, further comprising a controller configured to prevent the boring element from being activated by disabling the one or more user control devices associated with the boring element if the one or more sensors do not indicate that the distal end is proximate to the tissue surface.

9. The delivery device of claim 1, further comprising a cryotherapy delivery feature configured to cryo-ablate target nerve to reduce a symptom of rhinitis after delivery of the therapeutic agent.

10. The delivery device of claim 1, wherein the one or more user control devices comprise at least one device selected from a group consisting of: a trigger, a knob, a button, a switch, a lever, and/or a dial on the handpiece.

11. The delivery device of claim 1, wherein the therapeutic agent delivery member comprises a lumen of the needle.

12. The delivery device of claim 1, wherein the therapeutic agent delivery member comprises a delivery conduit that is separate and distinct from the needle.

* * * * *